United States Patent
Anthony et al.

(10) Patent No.: US 7,393,873 B2
(45) Date of Patent: Jul. 1, 2008

(54) ARYLSULFONAMIDE DERIVATIVES

(75) Inventors: Neville J. Anthony, Chalfont, PA (US); John Jin Lim, Perkiomenville, PA (US); Dai-shi Su, Dresher, PA (US); Michael R. Wood, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 166 days.

(21) Appl. No.: 10/561,319

(22) PCT Filed: Jun. 30, 2004

(86) PCT No.: PCT/US2004/021018

§ 371 (c)(1), (2), (4) Date: Dec. 20, 2005

(87) PCT Pub. No.: WO2005/004810

PCT Pub. Date: Jan. 20, 2005

(65) Prior Publication Data

US 2006/0142612 A1    Jun. 29, 2006

Related U.S. Application Data

(60) Provisional application No. 60/484,498, filed on Jul. 2, 2003.

(51) Int. Cl.
*A61K 31/18* (2006.01)
*C07C 311/15* (2006.01)
*C07C 311/21* (2006.01)

(52) U.S. Cl. ............ 514/603; 514/256; 514/317; 514/327; 514/331; 514/534; 514/601; 514/604; 546/293; 546/298; 560/9; 560/18; 560/27; 560/48; 564/80; 564/86; 564/88; 564/92

(58) Field of Classification Search ............ None
See application file for complete search history.

(56) References Cited

U.S. PATENT DOCUMENTS 5,250,549 A * 10/1993 Yoshino et al. ............ 514/345
6,403,607 B1    6/2002 Hidaka et al.
7,238,717 B2 * 7/2007 Fleming et al. ............ 514/350
2002/0061599 A1 * 5/2002 Elling et al. ............ 436/518

FOREIGN PATENT DOCUMENTS

DE    03544409        10/1986
FR    2290431     *   6/1976
WO    WO 95/33461     12/1995
WO    WO 03/099773    12/2003

OTHER PUBLICATIONS

Derwent abstract of FR 2290431A, Jul. 1976.*
CAS Abstract 1988: 131304 (1988).
CAS Registry No. 392305-40-7 (Feb. 2002).
Xiaohui Du, et al., *Chemistry & Biology*, 7 (9), pp. 733-742, (2000).
S. Rajagopalan, et al., *Proc. Indian Acad. Sci. Sect. A.*, 15 (15), pp. 432-436, (1941).
Milton C. Kloetzel, et al., *Journal of Medicinal and Pharmaceutical Chemistry*, 1(3), pp. 197-211, (1959).

* cited by examiner

*Primary Examiner*—Rosalynd Keys
(74) *Attorney, Agent, or Firm*—Mollie M. Yang; Valerie J. Camara

(57) ABSTRACT

N-aryl arylsulfonamide derivatives are bradykinin B1 antagonists or inverse agonists useful in the treatment or prevention of symptoms such as pain and inflammation associated with the bradykinin B1 pathway.

11 Claims, No Drawings

ARYLSULFONAMIDE DERIVATIVES

CROSS REFERENCE TO RELATED APPLICATIONS

This application is the National Stage of International Application No. PCT/US2004/021018, filed 30 Jun. 2004 which claims the benefit under 35 U.S.C. 119(e) of U.S. Provisional Application No. 60/484,498, filed 2 Jul. 2003.

BACKGROUND OF THE INVENTION

This invention is directed to arylsulfonamide compounds. In particular, this invention is directed to arylslulfonamide compounds that are bradykinin antagonists or inverse agonists.

Bradykinin ("BK") is a kinin which plays an important role in the pathophysiological processes accompanying acute and chronic pain and inflammation. Bradykinin (BK), like other kinins, is an autacoid peptide produced by the catalytic action of kallikrein enzymes on plasma and tissue precursors termed kininogens. The biological actions of BK are mediated by at least two major G-protein-coupled BK receptors termed B1 and B2. It is generally believed that B2 receptors, but not B1 receptors, are expressed in normal tissues and that inflammation, tissue damage or bacterial infection can rapidly induce B1 receptor expression. This makes the B1 receptor a particularly attractive drug target. The putative role of kinins, and specifically BK, in the management of pain and inflammation has provided the impetus for developing potent and selective BK antagonists. In recent years, this effort has been heightened with the expectation that useful therapeutic agents with analgesic and anti-inflammatory properties would provide relief from maladies mediated through a BK receptor pathway (see e.g., M. G. Bock and J. Longmore, *Current Opinion in Chem. Biol.,* 4:401-406(2000)). Accordingly, there is a need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools (in vivo and in vitro).

Chemical Abstracts No. 108:131304 (1988; German Patent Application DE3544409) discloses compounds of the formula:

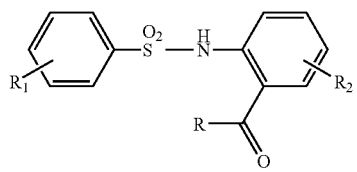

as inhibitors of cyclooxygenase and lipoxygenase. The compound N-[4-[[(2-benzoylphenyl)amino]-sulfonyl]phenyl]acetamide is specifically disclosed.

U.S. Pat. No. 6,403,607 discloses compounds of the formula:

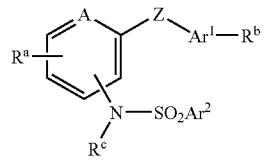

useful as treatment for peptic ulcers.

WO 95/33461 discloses anti-inflammatory compounds of the formula:

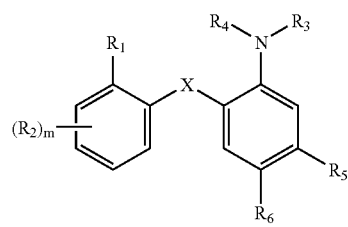

Du et al., *Chemistry & Biology,* 2000, 7(9):733-742 discloses the compound

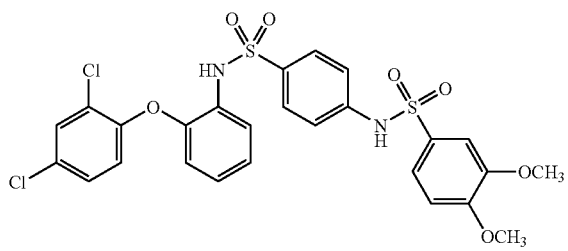

Kloetzel et al., *J. Med. Pharm. Chem.,* 1959, 1:197-211 discloses the compound

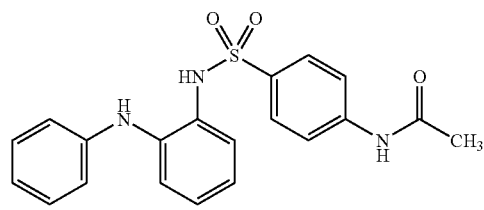

In *Proc. Indian Acad. Sci. Sect. A,* 15, 1942, p. 432-end, there is disclosed the compound

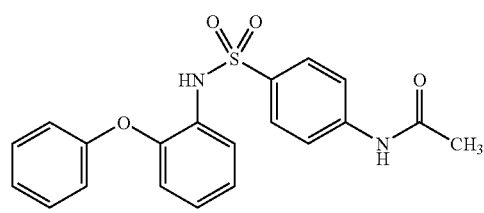

The compound N-[4-[[(2-benzoyl-4-chlorophenyl)amino]sulfonyl]phenyl]acetamide is registered with Chemical Abstracts Services as CAS RN 392305-40-7.

PCT Published Application WO03/099773 discloses CCR9 inhibitors of the formula:

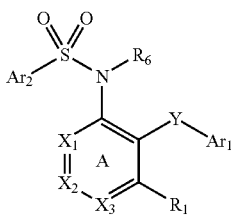

SUMMARY OF THE INVENTION

The present invention provides arylsulfonamide derivatives which are bradykinin antagonists or inverse agonists, pharmaceutical compositions containing such compounds, and methods of using them as therapeutic agents.

DETAILED DESCRIPTION OF THE INVENTION

In one aspect the present invention provides compounds of formula I or pharmaceutically acceptable salts thereof:

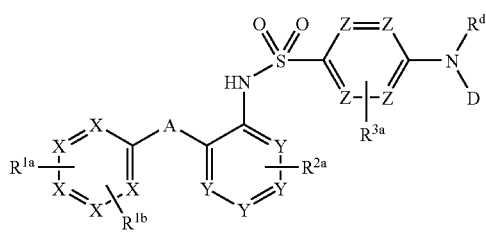

wherein

A is O, CO, S, $NR^d$, or $CR^bR^c$;

D is $COR^4$, $C(O)NR^dR^4$, $C(O)OR^4$, $SO_2R^{4t}$, $SO_2NR^dR^4$;

X, Y and Z are independently a ring carbon atom or a ring nitrogen atom, with the proviso that 0-3 X, 0-3 Y and 0-3 Z are ring nitrogen atoms;

$R^{1a}$ and $R^{1b}$ are independently selected from (1) H, (2) halogen, (3) $C_{1-6}$alkyl optionally substituted with 1-5 groups independently selected from halogen, nitro, cyano, $COR^a$, $CO_2R^a$, $C(O)NR^dR^e$, $OR^a$, $OC(O)R^a$, $SR^a$, $SO_2R^f$, $S(O)R^f$, $NR^dR^e$, $NR^dC(O)R^a$ and $NR^dSO_2R^f$, (4) $C(O)R^a$, (5) $CO_2R^a$, (6) $C(O)NR^dR^e$, (7) $OR^a$, (8) $OC(O)R^a$, (9) $OC(O)NR^dR^e$, (10) $NR^dR^e$, (11) $NR^dC(O)R^a$, (12) $NR^dC(O)OR^a$, (13) $NR^dC(O)NR^dR^e$, (14) $NR^dSO_2R^f$, (15) $SR^a$, (16) $S(O)R^f$, (17) $SO_2R^f$, (18) $SO_2NR^dR^e$, (19) CN, (20) $NO_2$, (21) optionally substituted aryl, (22) optionally substituted heteroaryl, (23) optionally substituted heterocyclyl, (24) optionally substituted aryl-$C_{1-6}$alkyl, (25) optionally substituted heteroaryl-$C_{1-6}$alkyl, and (26) optionally substituted heterocyclyl-$C_{1-6}$alkyl; wherein the substituents for aryl, heteroaryl, heterocyclyl, aralkyl, heteroaralkyl and heterocyclylalkyl are 1 to 3 groups independently selected from halogen, cyano, nitro, $OR^a$, $NR^dR^e$, $NR^dC(O)R^a$, $NR^dSO_2R^f$, $OC(O)R^a$, $NR^dC(O)_2R^a$, $SR^a$, $SO_2R^f$, oxo (for heterocyclyl and heterocyclylalkyl), $C(O)R^a$, $C(O)_2R^a$, $C_{1-4}$alkyloxy, aryl, aryl-$C_{1-4}$alkyl, heteroaryl, heteroaryl-$C_{1-4}$alkyl, $C_{3-6}$cycloalkyl and $C_{1-4}$alkyl optionally substituted with 1 to 5 halogen atoms, or $R^{1a}$, $R^{1b}$ and adjacent carbon atoms to which they are attached together form a saturated, partially unsaturated or aromatic 5- or 6-membered ring containing 0 to 2 heteroatoms selected from N, N—$R^g$, O and S;

$R^{2a}$ and $R^{3a}$ are independently selected from (1) H, (2) halogen, (3) $OR^a$, (4) $NR^dR^e$, (5) CN, (6) $NO_2$, (7) $CO_2R^a$, (8) $COR^a$, and (9) $C_{1-4}$alkyl optionally substituted with 1 to 5 halogen atoms, $R^4$ is selected from (1) H, (2) $C_{1-6}$alkyl optionally substituted with 1 to 5 groups independently selected from halogen, nitro, cyano, $C_{3-6}$cycloalkyl, $COR^a$, $CO_2R^a$, $C(O)NR^dR^e$, $OR^a$, $OC(O)R^a$, $SR^a$, $SO_2R^f$, $S(O)R^f$, $NR^dR^e$, $NR^dC(O)R^a$, $NR^dSO_2R^f$, and $NR^dC(O)_2R^a$, (3) optionally substituted $C_{3-6}$cycloalkyl, (4) $COR^a$, (5) $COOR^a$, (6) optionally substituted aryl, (7) optionally substituted heteroaryl, (8) optionally substituted heterocyclyl, (9) optionally substituted aryl-$C_{1-6}$alkyl, (10) optionally substituted heteroaryl-$C_{1-6}$alkyl, and (11) optionally substituted heterocyclyl-$C_{1-6}$alkyl; wherein the substituents for cycloalkyl, aryl, heteroaryl, heterocyclyl, aralkyl, heteroaralkyl and heterocyclylalkyl are 1 to 3 groups independently selected from halogen, cyano, nitro, $OR^a$, $NR^dR^e$, $NR^dC(O)R^a$, $NR^dSO_2R^f$, $OC(O)R^a$, $NR^dC(O)_2R^a$, $SR^a$, $SO_2R^f$, oxo (for heterocyclyl and heterocyclylalkyl), $C(O)R^a$, $C(O)_2R^a$, $C_{1-4}$alkyloxy, aryl optionally substituted with 1 or 2 halogen atoms, aryl-$C_{1-4}$alkyl, heteroaryl, heteroaryl-$C_{1-4}$alkyl, $C_{3-6}$cycloalkyl and $C_{1-4}$alkyl optionally substituted with 1 to 5 halogen atoms;

$R^{4t}$ is a group selected from $R^4$ except $R^{4t}$ is not H;

$R^a$ is (1) H, (2) $C_{1-6}$alkyl optionally substituted with 1 to 5 groups independently selected from halogen, cyano, nitro, OH, $C_{1-4}$alkyloxy and $C_{3-6}$cycloalkyl, (3) $C_{3-6}$cycloalkyl, (4) optionally substituted aryl, (5) optionally substituted heteroaryl, (6) optionally substituted heterocyclyl, (7) optionally substituted aryl-$C_{1-6}$alkyl, (8) optionally substituted heteroaryl-$C_{1-6}$alkyl, and (9) optionally substituted heterocyclyl-$C_{1-6}$alkyl; wherein the substituents for aryl, heteroaryl, heterocyclyl, aralkyl, heteroaralkyl and heterocyclylalkyl are 1 to 3 groups independently selected from halogen, cyano, nitro, $OR^g$, $NR^dR^e$, $NR^dC(O)R^g$, $NR^dSO_2R^f$, $OC(O)R^g$, $NR^dC(O)_2R^g$, $SR^g$, $SO_2R^f$, oxo (for heterocyclyl and heterocyclylalkyl), $C(O)Rg^a$, $C(O)_2R^g$, $C_{1-4}$alkyloxy, aryl, aryl-$C_{1-4}$alkyl, heteroaryl, heteroaryl-$C_{1-4}$alkyl, $C_{3-6}$cycloalkyl and $C_{1-4}$alkyl optionally substituted with 1 to 5 halogen atoms;

$R^b$ and $R^c$ are independently selected from H, halogen, or $C_{1-4}$alkyl optionally substituted with 1 to 5 halogen atoms;

$R^d$ and $R^e$ are independently selected from (1) H, (2) $C_{1-4}$alkyl, optionally substituted with 1 to 5 groups independently selected from halogen, amino, mono-$C_{1-4}$alkylamino, di-$C_{1-4}$alkylamino, and $SO_2R^f$, (3) aryl-$C_{1-6}$alkyl optionally substituted with 1 to 3 groups selected from halogen, cyano, nitro, OH, $C_{1-4}$alkyloxy, $C_{3-6}$cycloalkyl and $C_{1-4}$alkyl optionally substituted with 1 to 5 halogen atoms, (4) heteroaryl-$C_{1-6}$alkyl optionally substituted with 1 to 3 groups selected from halogen, cyano, nitro, OH, $C_{1-4}$alkyloxy, $C_{3-6}$cycloalkyl and $C_{1-4}$alkyl optionally substituted with 1 to 5 halogen atoms,and (5) $C_{3-6}$cycloalkyl, or $R^d$ and $R^e$, or $R^d$ and $R^4$, or $R^d$ and $R^{4t}$, together with the atom or atoms to which they are attached, complete a 4- to 8-membered saturated, partially saturated or aromatic ring optionally containing 1 to 3 heteroatoms independently selected from N, $NR^g$, O, S, and $SO_2$, and said ring being optionally fused to a benzene or a 5- or 6-membered heteraromatic ring, and optionally substituted with 1 to 3 substituents independently selected from halogen, cyano, nitro, $OR^g$, oxo, $C_{3-6}$cycloalkyl, aryl, aryl-$C_{1-4}$alkyl, heteroaryl, $NR^gR^g$, $NR^gCOR^g$, $NR^gCO_2R^g$ and $C_{1-4}$alkyl optionally substituted with 1 to 5 halogen atoms;

$R^f$ is selected from (1) $C_{1-4}$alkyl optionally substituted with 1 to 5 halogen atoms, (2) $C_{1-4}$alkyloxy, and (3) aryl optionally substituted with 1 to 3 groups selected from halogen, cyano, nitro, OH, $C_{1-4}$alkyloxy, $C_{3-6}$cycloalkyl and $C_{1-4}$alkyl optionally substituted with 1 to 5 halogen atoms;

$R^g$ is selected from (1) H, (2) $C_{1-4}$alkyl, (3) aryl, (4) aryl-$C_{1-6}$alkyl, (5) $C(O)_2C_{1-4}$alkyl and (6) $C(O)C_{1-4}$alkyl;

with the proviso that when each occurrence of X, Y and Z is a ring carbon atom, $R^{1a}$ and $R^{1b}$ are each hydrogen or chlorine, and $R^{2a}$ and $R^{2b}$ are each hydrogen, then D is not $NHC(O)C_{1-6}$alkyl; with the further proviso that the following compound is excluded:

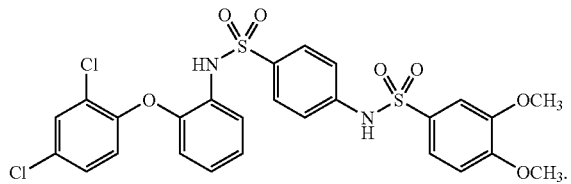

In one embodiment of the compounds of formula I, A is C(O), O or S. In one subset thereof, A is C(O) or O.

In a second embodiment one of Y is a ring nitrogen or carbon atom and the others are ring carbon atoms, or one of Z is a ring nitrogen or carbon atom and the others are ring carbon atoms.

In a third embodiment one of X is a ring nitrogen or carbon atom and the others are ring carbon atoms. In one subset thereof, each occurrence of Z and each occurrence of Y is a ring carbon atom. In a second subset thereof each occurrence of X, Y and Z is a ring carbon atom.

In a fourth embodiment of the compounds of formula I, D is $COR^4$, $C(O)NR^dR^4$ or $C(O)OR^4$. In one subset $R^4$ is selected from (1) $C_{1-6}$alkyl optionally substituted with 1 to 5 halogen atoms, $OR^a$, $NR^dR^e$ or $C(O)NR^dR^e$ in which $R^d$ and $R^e$ (of $NR^dR^e$ and $NR^dR^e$) together with the nitrogen to which they are attached complete a 4- to 8-membered ring optionally containing an additional heteroatom selected from $NR^g$, O, S, and $SO_2$, and said ring being optionally fused to a benzene or a 5- or 6-membered heteraromatic ring, and optionally substituted with 1 to 3 substituents independently selected from halogen, cyano, nitro, $OR^g$, oxo, $C_{3-6}$cycloalkyl, aryl, heteroaryl, $NR^gR^g$, $NR^gCOR^g$, $NR^gCO_2R^g$ and $C_{1-4}$alkyl optionally substituted with 1 to 5 halogen atoms; (2) optionally substituted heteroaryl; (3) optionally substituted heteroaryl-$C_{1-4}$alkyl; (4) optionally substituted heterocyclyl; and (5) optionally substituted heterocyclyl-$C_{1-4}$alkyl; wherein the substituents for heteroaryl, heteroaralkyl, heterocyclyl and heterocyclylalkyl are 1 to 3 groups independently selected from halogen, cyano, nitro, $OR^a$, $NR^dR^e$, $NR^dC(O)R^a$, $NR^dSO_2R^f$, $OC(O)R^a$, $NR^dC(O)_2R^a$, $SR^a$, $SO_2R^f$, oxo (for heterocyclyl and heterocyclylalkyl), $C(O)R^a$, $C(O)_2R^a$, $C_{1-4}$alkyloxy, aryl, aryl-$C_{1-4}$alkyl, heteroaryl, heteroaryl-$C_{1-4}$alkyl, $C_{3-6}$cycloalkyl and $C_{1-4}$alkyl optionally substituted with 1 to 5 halogen atoms.

In a fifth embodiment of the compounds of formula I are compounds of formula Ia and pharmaceutically acceptable salts thereof:

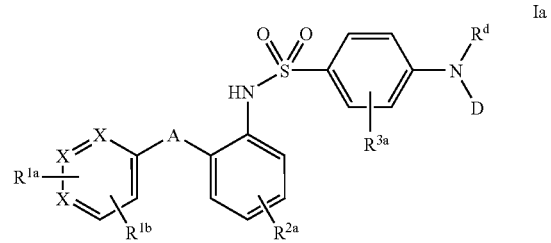

and pharmaceutically acceptable salts thereof; wherein
A is O or C(O);
one of X is a ring carbon or nitrogen atom, and the others are ring carbon atoms;
D is $C(O)R^4$, $C(O)NR^dR^4$ or $C(O)OR^4$;
$R^{1a}$ and $R^{1b}$ are independently selected from hydrogen, halogen, $C_{1-4}$alkyl, cyano, $SR^a$, $OR^a$ and $CF_3$;
$R^{2a}$ and $R^{3a}$ are independently H or halogen;
$R^4$, $R^a$ and $R^d$ are as defined under formula I.

In one subset of formula Ia are compounds wherein D is $C(O)R^4$, and $R^4$ is selected from (1) $C_{1-4}$alkyl substituted with one to 5 groups independently selected from halogen, $C_{3-6}$cycloalkyl, $NR^dR^e$, $NR^dC(O)_2R^a$, $C(O)NR^dR^e$, $C(O)OR^a$, and $OR^a$; (2) $C_{3-6}$cycloalkyl; (3) phenyl; (4) phenyl-$C_{1-4}$alkyl; (5) optionally substituted heteroaryl; (6) optionally substituted heteroaryl-$C_{1-4}$alkyl; (7) optionally substituted heterocyclyl; (8) optionally substituted heterocyclyl-$C_{1-4}$alkyl; and (9) $COOR^a$; wherein heteroaryl, including as part of heteroarylalkyl, is selected from benzofuranyl, pyrazolo[1.5-a]pyrimidinyl, 1-azindolizinyl, s-triazolo[pyrimisinyl, thie[3.2b]pyridinyl, isoxazolyl, pyrazinyl, pyrazolyl, pyrimidinyl, benzisoxazolyl, pyridyl, indolyl, benzimidazolyl, benzthiazolyl and imidazo[2, a-b]thiazolyl; heterocyclyl, including as part of heterocyclylalkyl, is selected from morpholinyl, tetrahydropyranyl, tetrahydrofuranyl, pyrrolidinyl, piperidinyl and imidazolidinyl; the substituents for heteroaryl is 1 or 2 groups independently selected from $C_{1-4}$alkyl, $C_{3-6}$cycloalkyl, heteroaryl optionally substituted with 1 or 2 halogen, aryl optionally substituted with 1 or 2 halogen, aryl-$C_{1-4}$alkyl, $CF_3$, and $OR^a$; and the substituents for heterocyclyl is 1 to 3 groups independently selected from oxo and $C_{1-4}$alkyl. In a preferred subset $R^4$ is $C_{1-4}$alkyl substituted with $NR^dR^e$ or $C(O)NR^dR^e$ in which $R^d$ and $R^e$ together with the nitrogen atom to which they are attached, complete an optionally substituted 5- or 6-membered saturated ring having 0 to 1 additional ring heteroatom selected from $NR^g$, O, S and $SO_2$, and wherein said substituent is 1 or 2 groups independently selected from $OR^a$, halogen, $C_{1-4}$alkyl and oxo.

In a second subset of formula Ia are compounds wherein D is $C(O)NR^dR^4$, wherein $R^d$ is H and $R^4$ is selected from (1) $C_{1-4}$alkyl substituted with a group selected from halogen, $OR^a$, $CO_2R^a$, $NHCOR^a$, $NR^dR^e$ and $C(O)NR^dR^e$; (2) optionally substituted heteroaryl-$C_{1-4}$alkyl wherein heteroaryl is selected from azaindolizinyl, imidazolyl, benzimidazolyl, pyrazinyl, pyridyl, indolyl, triazolyl, thiazolyl, imidazo[1,2-a]pyridyl, imidazo[1,2-a]pyrimidinyl, imidazo[2,1-b]thiazolyl, and pyrazolo[1,5-a]pyrimidinyl; (3) optionally substituted heterocyclyl-$C_{1-4}$alkyl wherein heterocyclyl is selected from tetrahydropyranyl, tetrahydrofuranyl and 1.4-dioxanyl; (4) optionally substituted heterocyclyl selected from pyrrolidinyl and piperidinyl; (5) $CO_2R^a$; (6) $C_{3-6}$cycloalkyl; and (7) optionally substitued phenyl-$C_{1-4}$alkyl; or wherein $R^d$ and $R^4$ together with the nitrogen atom to which they are attached complete an optionally substituted 5- or 6-membered saturated ring having 0 to 1 additional ring heteroatom selected fom $NR^g$, O, S and $SO_2$, wherein said ring is optionally fused to a benzene or a 5- or 6-membered heteroaryl ring, and said substituent is 1 or 2 groups independently selected from $OR^a$, halogen, $C_{1-4}$alkyl, $NR^dR^e$, $NR^dCO2R^a$, and oxo. In a preferred subset $R^d$ is H and $R^4$ is $C_{1-4}$alkyl substituted with $NR^dR^e$ or $C(O)NR^dR^e$, wherein $R^d$ and $R^e$ together complete (1) an optionally substituted 5- or 6-membered saturated ring having 0 to 1 additional ring heteroatom selected from $NR^g$, O, S and $SO_2$, and wherein said substituent is 1 or 2 groups independently selected from $OR^a$, halogen, $C_{1-4}$alkyl and oxo; or (2) an optionally substituted 5-membered aromatic ring having 0 to 2 additional heteroatoms selected from N, O and S, and wherein said ring is optionally benzofused and said substituent is 1 or 2 groups independently selected from $OR^a$, halogen and $C_{1-4}$alkyl.

In a third subset of formula Ia are compounds wherein D is $C(O)OR^4$, and $R^4$ is selected from (1) $C_{2-4}$alkyl substituted with $NR^dR^e$ or $C(O)NR^dR^e$ in which (1) $R^d$ and $R^e$ together with the nitrogen atom to which they are attached complete an optionally substituted 5- or 6-membered saturated ring having 0 to 1 additional ring heteroatom selected from NR, O, S and $SO_2$, and wherein said substituent is 1 or 2 groups independently selected from $OR^a$, halogen, $C_{1-4}$alkyl and oxo; (2) optionally substituted heterocyclylalkyl wherein heterocyclyl is selected from tetrahydropyranyl, tetrahydrofuranyl, pyrrolidinyl, morpholinyl, oxazolidinyl and dioxolanyl; (3) furanyl-$C_{1-4}$alkyl; and (4) phenyl-$C_{1-4}$alkyl.

In a fourth subset of formula Ia are compounds wherein the group —$N(R^d)D$ is a 5- or 6-membered lactam, cyclic urea or cyclic carbamate, each of which is optionally substituted with $C_{1-4}$alkyl, benzyl or tetrahydrofuranylmethyl.

Unless otherwise stated, the following terms have the meanings indicated below:

"Alkyl" as well as other groups having the prefix "alk" such as, for example, alkoxy, alkanoyl, alkenyl, alkynyl and the like, means carbon chains which may be linear or branched or combinations thereof, and having the designated number of carbon atoms. Examples of alkyl groups include methyl, ethyl, propyl, isopropyl, butyl, sec- and tert-butyl, pentyl, hexyl, heptyl and the like.

"Aryl" means a 6-14 membered carbocyclic aromatic ring system comprising 1-3 benzene rings. If two or more aromatic rings are present, then the rings are fused together, so that adjacent rings share a common bond. Examples include phenyl and naphthyl. "Aralkyl" or "arylalkyl" means the radical -(alkylene)-aryl; examples of aralkyl include benzyl, phenethyl, α-methylbenzyl, and the like.

"Cycloalkyl" means saturated carbocycles containing no heteroatoms, and having the designated number of ring carbon atoms. Examples of cycloalkyl include cyclopropyl, cyclobutyl, cyclopentyl, and cyclohexyl.

"Halogen" means fluorine, chlorine, bromine and iodine.

"Heteroaryl" means a monocyclic or bicyclic aromatic radical of 5 to 10 ring atoms containing 1 to 4 ring heteroatoms selected from N (including N-oxide), O, or S, the remaining ring atoms being carbon. In a bicyclic aromatic radical only one ring, containing a heteroatom, need to be aromatic. Examples of heteroaryl include pyridyl, pyrrolyl, pyrazolyl, imidazolyl, thienyl, furanyl, indolyl, indolizinyl, azaindolizinyl, quinolyl, pyrazinyl, pyrimidinyl, pyridazinyl, oxazolyl, isoxazolyl, benzoxazolyl, benzisoxazolyl, benzothiazolyl, isoquinolinyl, benzimidazolyl, benztriazolyl, benzofuranyl, benzothienyl, benzopyranyl, imidazo[2,1-b]thiazolyl, imidazo[1,2-a]pyridyl, imidazo[1,2-a]-pyrimidinyl, pyrazolo[1,5-a]pyridyl, imidazolyl, triazolyl, thiadiazolyl, oxadiazolyl, thiazolyl, triazolopyrimidinyl, pyrazolopyrimidinyl, thienopyridinyl, pyrrolopyridinyl 4,5,6,7-tetrahydrobenzisoxazolyl, indazolyl, 4,5,6,7-tetrahydroindazolyl, and 4,5,6,7-tetrahydrobenzothienyl. "Heteroaralkyl" or "heteroarylalkyl" means the radical -alkylene)-heteroaryl.

"Heterocyclyl" means a monocyclic or bicyclic radical that is fully saturated or partially saturated, containing 3 to 10 ring atoms at least one of which is selected from N—$R^g$ (including N-oxides), O, S and $S(O)_2$, wherein $R^g$ is as previously defined. Examples of heterocyclyl include aziridinyl, azetidinyl, pyrrolidinyl, piperidinyl, piperazinyl, morpholinyl, thiamorpholinyl, oxetanyl, tetrahydrofuranyl, tetrahydropyranyl, azepinyl, diazepinyl, dihydrobenzofuranyl, 1,2,3,4-tetrahydroquinolinyl, dioxanyl, dioxolanyl, imidazolinyl, imidazolidinyl, oxazolidinyl, 7-oxabicyclo[2.2.1]heptanyl, and the like. "Heterocyclylalkyl" means the radical -(alkylene)-heterocyclyl.

"Optionally substituted" is intended to include both substituted and unsubstituted. Thus, for example, optionally substituted aryl could represent a pentafluorophenyl or a phenyl ring.

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Prodrugs

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete, units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

| Inj. Suspension (I.M.) | mg/mL | Tablet | mg/tab. | Capsule | mg/cap. |
| --- | --- | --- | --- | --- | --- |
| Cmpd of Formula I | 10 | Cmpd of Formula I | 25 | Cmpd of Formula I | 25 |
| Methylcellulose | 5.0 | Microcryst. Cellulose | 415 | Lactose Powder | 573.5 |
| Tween 80 | 0.5 | Povidone | 14.0 | Magnesium Stearate | 1.5 |
| Benzyl alcohol | 9.0 | Pregelatinized Starch | 43.5 | | 600 |
| Benzalkonium chloride | 1.0 | Magnesium Stearate | 2.5 | | |
| Water for injection to a total volume of 1 mL | | | 500 | | |

Utilities

Compounds of this invention are antagonists or inverse agonists of bradykinin receptor, in particular the bradykinin B1 receptor, and as such are useful in the treatment and prevention of diseases and conditions mediated through the bradykinin receptor pathway such as pain and inflammation. The present invention provides further the use of a compound of formula I in the manufacture of medicaments useful in the treatment or prevention of diseases or disorders mediated through the bradykinin receptor pathway. The compounds would be effective in the treatment or prevention of pain including, for example, visceral pain (such as pancreatitis, interstitial cystitis, renal colic, prostatitis, chronic pelvic pain), neuropathic pain (such as postherpetic neuralgia, acute zoster pain, nerve injury, the "dynias", e.g., vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (eg, postmastectomy syndrome, postthoracotomy syndrome, stump pain)), bone and joint pain (osteoarthritis), spine pain (e.g., acute and chronic low back pain, neck pain, spinal stenosis), shoulder pain, repetitive motion pain, acute pain such as dental pain, sore throat, cancer pain, myofascial pain (muscular injury, fibromyalgia), postoperative, perioperative pain and preemptive analgesia (including but not limited to general surgery, orthopedic, and gynecological), chronic pain, dysmenorrhea (primary and secodnary), as well as pain associated with angina, and inflammatory pain of varied origins (e.g. osteoarhritis, rheumatoid arthritis, rheumatic disease, teno-synovitis and gout, ankylosing spondylitis, bursitis).

Further, the compounds of this invention can also be used to treat hyperreactive airways and to treat inflammatory events associated with airways disease e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome". Compounds of the present invention may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including alumninosis, anthracosis, asbestosis, chalicosis, ptilosis, siderosis, silicosis, tabacosis and byssinosis.

Compounds of the present invention may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema. They may be used to treat diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, eg. Parkinson's and Alzheimers disease, epilepsy, septic shock e.g. as anti-hypovolenic and/or anti-hypotensive agents, headache including cluster headache, migraine including prophylactic and acute use, stroke, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

The compounds of this invention are useful in the treatment of pain and inflammation by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week The compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, oral surgery, gynecological), neuropathic pain (post-herpetic neuralgia), and chronic pain by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

In particular, inflammatory pain such as, for example, inflammatory airways disease (chronic obstructive pulmonary disease) would be effectively treated by the compounds of this invention by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Further, the compounds of this invention can additionally be used to treat asthma, inflammatory bowel disease, rhinitis, pancreatitis, cystitis (interstitial cystitis), uveitis, inflammatory skin disorders, rheumatoid arthritis and edema resulting from trauma associated with burns, sprains or fracture by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used subsequent to surgical intervention (e.g. as post-operative analgesics) and to treat inflammatory pain of varied origins (e.g. osteoarthritis, rheumatoid arthritis, rheumatic disease, teno-synovitis and gout) as well as for the treatment of pain associated with angina, menstruation or cancer by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat diabetic vasculopathy, post capillary resistance or diabetic symptoms associated with insulitis (e.g. hyperglycemia, diuresis, proteinuria and increased nitrite and kallilrein urinary excretion) by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week, They may be used to treat inflammatory skin disorders such as psoriasis and eczema by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used as smooth muscle relaxants for the treatment of spasm of the gastrointestinal tract or uterus or in the therapy of Crohn's disease, ulcerative colitis or pancreatitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Such compounds may be used therapeutically to treat hyperreactive airways and to treat inflammatory events associated with airways disease e.g. asthma, and to control, restrict or reverse airways hyperreactivity in asthma by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat intrinsic and extrinsic asthma including allergic asthma (atopic or non-atopic) as well as exercise-induced bronchoconstriction, occupational asthma, viral or bacterial exacerbated asthma, other non-allergic asthmas and "wheezy-infant syndrome" by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Additionally, they may be effective against liver disease, multiple sclerosis, atherosclerosis, Alzheimer's disease, septic shock e.g. as anti-hypovolemic and/or anti-hypotensive agents, cerebral edema, headache including cluster headache, migraine including prophylactic and acute use, closed head trauma, irritable bowel syndrome and nephritis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) morphine and other opiate receptor agonists including propoxyphene (Darvon) and tramadol; (2) non-steroidal antiinflammatory drugs (NSAIDs) including COX-2 inhibitors such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib); (3) corticosteroids such as betamethasone, budesonide, cortisone, dexamethasone, hydrocortisone, methylprednisolone, prednisolone, prednisone and triamcinolone; (4) histamine HI receptor antagonists such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, desloratadine, fexofenadine and levocetirizine; (5) histamine H2 receptor antagonists such as cimetidine, famotidine and ranitidine; (6) proton pump inhibitors such as omeprazole, pantoprazole and esomeprazole; (7) leukotriene antagonists and 5-lipoxygenase inhibitors such as zafirlukast, montelukast, pranlukast and zileuton; (8) drugs used for angina, myocardial ischemia including nitrates such as nitroglycerin and isosorbide nitrates, beta blockers such as atenolol, metoprolol, propranolol, acebutolol, betaxolol, bisoprolol, carteolol, labetalol, nadolol, oxprenolol, penbutolol, pindolol, sotalol and timolol, and calcium channel blockers such as diltiazam, verapamil, nifedipine, bepridil, felodipine, flunarizine, isradipine, nicardipine and nimodipine; (9) incontinence medications such as antimuscarinics, e.g., tolterodine and oxybutinin); (10) gastrointestinal antispasmodics (such as atropine, scopolamine, dicyclomine, antimuscarinics, as well as diphenoxylate); skeletal muscle relaxants (cyclobenzaprine, carisoprodol, chlorphenesin, chlorzoxazone, metaxalone, methocarbamol, baclofen, dantrolene, diazepam, or orphenadrine); (11) gout medications such as allopurinol, probenicid and colchicine; (12) drugs for rheumatoid arthritis such as methotrexate, auranofin, aurothioglucose and gold sodium thiomalate; (13) drugs for osteoporosis such as alendronate and raloxifene; decongestants such as pseudoephedrine and phenylpropanolamine; (14) local anesthetics; (15) anti-herpes drugs such as acyclovir, valacyclovir and famcyclovir; (16) anti-emetics such as ondansetron and granisetron; (17) migraine drugs such as the triptans (e.g. rizatriptan, sumatriptan), ergotamine, dihydroergotamine, CGRP antagonists, antidepressants (e.g., tricyclic antidepressants, serotonin-selective reuptake inhibitors, beta-adrenergic blockers); (18) VR1 aniagonsits; (19) anti-convulsants (e.g., gabapentin, pregabalin, lamotrigine, topiramate, carbamazepine, oxcarbazepine, phenytoin); (20) glutamate antagonists (e.g., ketamine and other NMDA antagonists, NR2B antagonists); (21) acetaminophen; (22) CCR2 antagonists; (23) PDE4 antagonists.

Biological Evaluation

Assessing the Affinity of Selected Compounds to Bind to the Bradykinin B1 or B2 Receptor. Radioligand binding assays are performed using membranes from CHO cells that stably express the human, rabbit, rat, or dog B1 receptors or CHO cells that express the human B2 receptor. For all receptor types, cells are harvested from culture flasks in PBS/I mM EDTA and centrifuged at 1000×g for 10 minutes. The cell pellets are homogenized with a polytron in ice cold 20 mM BEPES, 1 mM EDTA, pH 7.4 (lysis buffer) and centrifuged at 20,000×g for 20 minutes. The membrane pellets are rehomogenized in lysis buffer, centrifuged again at 20,000×g and the final pellets are resuspended at 5 mg protein/ml in assay buffer (120 mM NaCl, 5 mM KCl, 20 mM HEPES, pH 7.4) supplemented with 1% BSA and frozen at −80° C.

On the day of assay, membranes are centrifuged at 14,000×g for 5 minutes and resuspended to the desired protein concentration in assay buffer containing 100 nM enaliprilat, 140 µg/mL bacitracin and 0.1% BSA. 3H-des-arg10, leu9 kallidin is the radioligand used for the human and rabbit B1 receptors, 3H-des-arg10 kailidin is used for the rat and dog B1 receptors, and 3H-bradykinin is used to label the human B2 receptor.

For all assays, compounds are diluted from DMSO stock solutions with 4 µL added to assay tubes for a final DMSO concentration of 2%. This is followed by the addition of 100 µL radioligand and 100 µL of the membrane suspension. Nonspecific binding for the B1 receptor binding assays is determined using 1 μM des-arg10 kallidin and nonspecific binding for the B2 receptor is determined with 1 μM bradykinin. Tubes are incubated at room temperature (22° C.) for 60 minutes followed by filtration using a Tomtec 96-well harvesting system. Radioactivity retained by the filter is counted using a Wallac Beta-plate scintillation counter.

Assay for Bradykinin B1 Antagonists. B1 agonist-induced calcium mobilization was monitored using a Fluorescence Imaging Plate Reader (FLIPR). CHO cells expressing the B1 receptor were plated in 96 or 384 well plates and allowed to incubate in Iscove's modified DMEM overnight. Wells were washed two times with a physiological buffered salt solution and then incubated with 4 uM Fluo-3 for one hour at 37° C. The plates were then washed two times with buffered salt solution and 100 uL of buffer was added to each well. Plates were placed in the FLIPR unit and allowed to equilibrate for two minutes. The test compound was then added in 50 ul volumes followed five minutes later by 50 ul of agonist (des-arg$^{10}$ kallidin). Relative fluorescence peak heights in the absence and presence of antagonist were used to calculate the degree of inhibition of the B1 receptor agonist response by the test compound. Eight to ten concentrations of test compound were typically evaluated to construct an inhibition curve and determine IC50 values using a four-parameter nonlinear regression curve fitting routine.

Assay for Bradykinin Inverse Agonists. Inverse agonist activity at the human B1 receptor was evaluated using transiently transfected HEK293 cells. One day following transfection cell flasks were labeled overnight with 6 uCi/ml [$^3$H] myo-inositol. On the day of assay, the media was removed and the attached cells were gently rinsed with 2×20 ml of phosphate-buffered saline. Assay buffer (HEPES buffered physiological salts, pH 7.4) was added and the cells were detached by tapping of the flask. The cells were centrifuged at 800×g for five minutes and resuspended at 1×10$^6$ cells/ml in assay buffer supplemented with 10 mM lithium chloride. After 10 minutes at room temperature, one-half ml aliquots were distributed to tubes containing test compound or vehicle. After an additional 10 minutes the tubes were transferred to a 37° C. water bath for 30 minutes. The incubation was terminated by the addition of a 12% perchloric acid solution and the tubes were placed on ice for 30 minutes. The acid was then neutralized with KOH and the tubes centrifuged to pellet precipitated material. [$^3$H]Inositol monophosphate formed was recovered by standard ion exchange chromatographic techniques and quantitated by liquid scintillation counting. Inverse agonist activity was determined by the degree to which a test compound reduced basal (cells incubated with vehicle) levels of [$^3$H]ionositol monophosphate accumulation.

Abbreviations Used

The following abbreviations have the meanings indicated, unless stated otherwise in the specification: AcCN=acetonitrile; BOC (boc)=t-butyloxycarbonyl; DCM=dichloromethane; DMF=dimethylformamide; DMSO=Dimethyl sulfoxide; EDC or EDCI=1-(3-dimethylaminopropyl)3-ethylcarbodiimide HCl; eq.=equivalent(s); ES (or ESI)-MS=electron spray ionization–mass spectroscopy; Et=ethyl; EtOAc=ethyl acetate; EtOH=ethanol; FAB-MS=fast atom bombardment-mass spectroscopy; HMPA=hexamethylphosphoramide; HOAt=1-hydroxy-7-azabenzotriazole; HOBt=1-hydroxybenzotriazole hydrate; HPLC=high pressure liquid chromatography; LCMS=liquid chromatography/mass spectroscopy; LiHMDS=lithium bis(trimethylsilyl)amide; Me=methyl; MeOH=methanol; MHz-megahertz; MsCl=mesyl chloride; NEt$_3$=triethylamine; NMR=nuclear magnetic resonance; TFA=trifluoroacetic acid; TBF=tetrahydrofuran Compounds of formula I may be prepared according to the following illustative schemes. The starting materials used in the synthesis of compounds of formula I or Ia are commercially available, known in the literature, or readily prepared from available chemicals in accordance with conventional synthetic methods well known to those skilled in the art. Both the schemes and specific examples provided herein are for illustrative purpose, and a person skilled in the art will appreciate that other compounds of the present invention may be analogously prepared using the illustrative procedures, or they may be obtained from exemplified compounds via functional group interconversion procedures that are generally known in the art, or they may be prepared by other procedures that are known to persons skilled in the art of organic synthesis.

As illustrated in Scheme 1, compounds of formula I may be prepared by reacting an arylamine 1 with a sulfonylating agent such as the sulfonyl chloride 2 in the presence of a base such as pyridine.

SCHEME 1

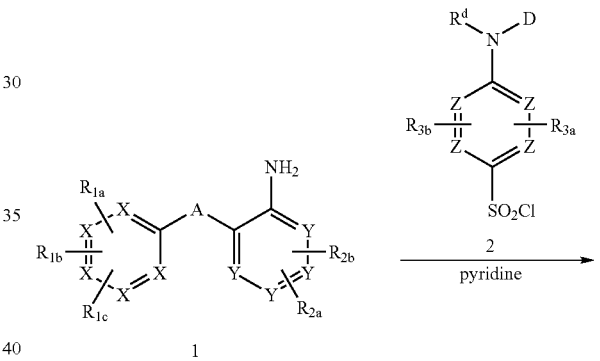

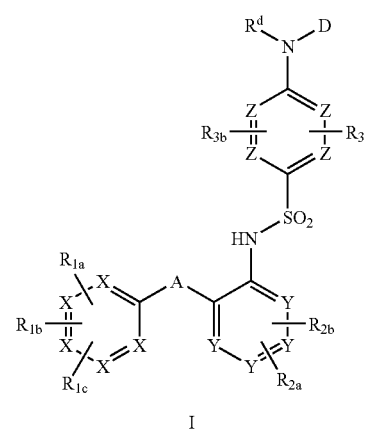

I

Alternatively, compounds of formula I may be prepared by the procedure illustrated in Scheme 2.

SCHEME 2

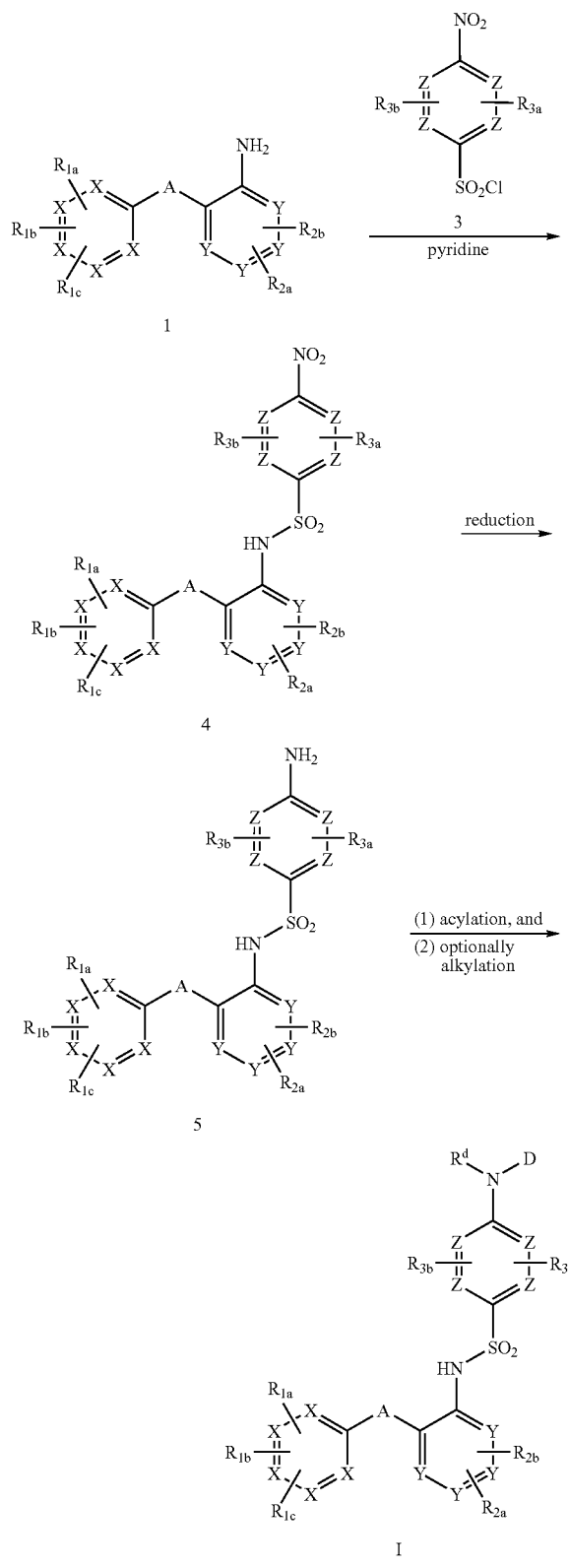

Arylamine 1 is coupled with the nitroarylsulfonyl chloride 3 to give the sulfonamide nitroarysulfonamide 4. Reduction with sodium dithionite or Fe/HCl provides the aminoarylsulfonamide 5, which upon acylation with an appropriate acid, acid chloride or anhydride gives the corresponding compound of formula I.

REFERENCE EXAMPLES 1.
4-Amino-N-(2-benzoylphenyl)benzenesulfonamide

2-Aminobenzophenone (20 mg) was dissolved in 1 mL of methylene chloride and 4-nitrobenzenesulfonyl chloride (34 mg, 1.5 equiv) was added thereto followed by pyridine (16 mL, 2 equiv). After 10 minutes the reaction mixture was oncentrated in vacuo, subjected to flash chromatography (eluting with 0% to 25% EtOAc/hexane) to provide N-(2-benzoylphenyl)-4-nitrobenzenesulfonamide. ESMS, M+H$^+$ found: 383.1.

The above nitrobenzenesulfonamide (500 mg) was dissolved in 10 mL of 2:2:1 EtOH/acetic acid/water and elemental iron (508 mg, 7.4 equiv) was added thereto followed by 5 uL of concentrated HCl. The reaction mixture was heated to 100° C. for 10 minutes, and then cooled to rt and diluted with 35 mL of water. The layers were separated and the aqueous layer was extracted three times with methylene chloride. The organic layer was washed twice with saturated sodium bicarbonate and twice with wate, back extracted once with methylene chloride, and dried over sodium sulfate, filtered, concentrated in vacuoto provide crude 4-amino-N-(2-benzoylphenyl)benzenesulfonamide, which was used without further purification. Purity was determined by LC/MS (ESMS, M+H$^+$ found: 353.1).

2. (2-Aminophenyl)(5-fluoropyridin-2-yl)methanone

2-Bromo-5-fluoropyridine (10 g, 56.8 mmol) and 2-aminobenzonitrile (5.6 g, 47.4 mmol) were dissolved in 100 mL of toluene and cooled to −30° C. To the resulting solution was added nBuLi (1.6 M in hexanes, 65 mL, 104 mmol, 2.2 equv) dropwise, and the reaction mixture was warmed to 0 deg for 90 minutes. The reaction mixture was then poured into 100 mL of cooled 3N HCl and stirred for 15 minutes, then 5N NaOH was added until the reaction mixture turned basic. The reaction mixture was extracted with $CH_2Cl_2$ (3×100 ml), washed with brine (1×100 mL), dried over sodium sulfate, filtered, and concentrated in vacuo. Flash chromatography (0% to 30% EtOAc/hexanes) gave the title compound as a solid (LC/MS found: 217.2)

3. N-[4-({[2-(2,4-dichlorophenoxy)phenyl]amino}sulfonyl)phenyl]acetamide

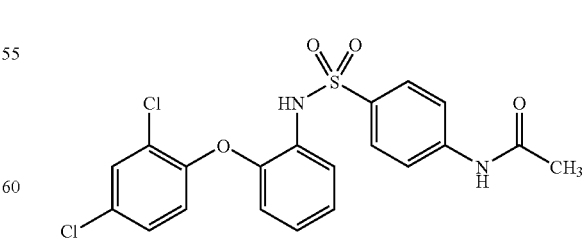

A mixture of 2-(2,4-dichlorophenoxy)aniline HCl (0.659 g, 2.27 mmol) and 4-(acetyl-amino)benzenesulfonyl chloride (0.500 g, 2.14 mmol) in 2 mL pyridine was stirred at room temperature overnight. The mixture was partitioned between ethyl acetate and 0.5 N HCl. The organic layer was washed with water (×2), half brine, and then brine. The organic layer was dried over sodium sulfate, filtered, and evaporated under reduced pressure to obtain a residue as a solid. The solid was titrated with 1% MeOH in DCM to provide the title compound that gave proton NMR spectra consistent with theory and a mass ion (ES) of 451.0 for M+H$^+$. $^1$H NMR (400 M , CD$_3$OD) δ 7.63 (m, 3H), 7.55 (bd, J=8.8 Hz, 2H), 7.47 (d, J=2.8 Hz, 1H), 7.14-7.06 (m, 3H), 6.56 (m, 1H), 6.36 (d, J=8.8 Hz, 1H), 2.14 (s, 3H).

The following examples are provided to illustrate the invention without limiting the invention to the particulars of these examples.

EXAMPLE 1

N-(4-{[(2-(2,4-dichloro)phenoxy)-6-fluorophenyl)amino]sulfonyl}phenyl)acetamide

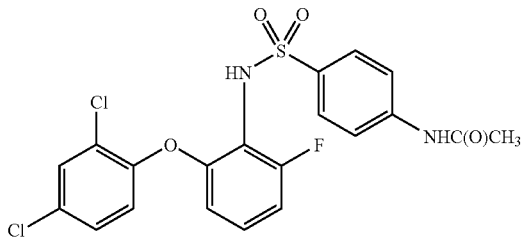

Under a nitrogen atmosphere, 2,4-dichlorophenol (500 mg, 3.067 mmol) was diluted in DMF (15 mL). Cesium carbonate (3 g, 9.202 mmol) was then added followed by 2,5-difluoronitro-benzene (976 mg, 6.135 mmol). The reaction was heated to 90° C. and allowed to stir for 12 hours. Then, 500 uL of water was added and was heated for an additional 4 hours. The reaction was then quenched with water (30 mL) and extracted with ethyl acetate (3×60 mL). The organic extracts were dried over sodium sulfate and concentrated. Silica gel chromatography (5%-20% EtOAc/hexanes) gave 1-(2,4-dichlorophenoxy)-3-fluoro-2-nitrobenzene (257 mg, 30%).

Under a nitrogen atmosphere, the above compound (230 mg, 0.761 mmol) was diluted in methanol (7.5 mL). Then tin(II) chloride dihydrate (515 mg, 2.284 mmol) was added and the reaction was refluxed at 85° C. for 4 hours. The methanol was then evaporated off and the residue was dissolved in methylene chloride (6 mL). A saturated solution of sodium bicarbonate (12 mL) was added and the suspension was extracted with methylene chloride (3×12 mL). The organic extracts were dried over sodium sulfate and concentrated. Silica gel chromatography (5%-20% EtOAc/hexanes) gave 2-(2,4-dichlorophenoxy)-6-fluoroaniline (68 mg, 33%).

The title compound was prepared in a manner analogous to that described in Reference Example 3 using the above phenyl ether.

EXAMPLE 2

Methyl 2-{[2-({[4-(acetylamino)phenyl]sulfonyl}amino)phenyl]thio}benzoate

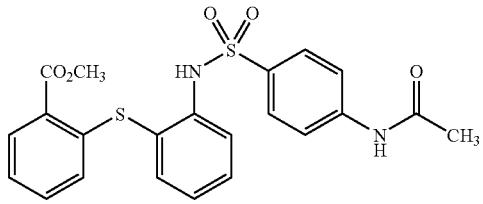

Step 1: Methyl 2-[(2-nitrophenyl)thio]benzoate

A mixture of methyl 2-mercaptobenzoate (0.656 g, 3.90 mmol), 1-fluoro-2-nitrobenzene (0.550 g, 3.90 mmol), and potassium carbonate (1.40 g, 10.1 mmol) in DMSO (10 mL) was stirred under nitrogen at room temperature overnight. The mixture was partitioned between water and diethyl ether, and the organic layer was washed with water (×2), half brine and brine. The organic layer was dried over sodium sulfate, filtered, and concentrated under reduced pressure to provide crude methyl 2-[(2-nitro-phenyl)thio]benzoate as a yellow solid that gave a mass ion (ES) of 290.1 for M+H$^+$.

Step 2: Methyl 2-[(2-aminophenyl)thio]benzoate

A solution of methyl 2-[(2-nitrophenyl)thio]benzoate (1.17 g, 4.04 mmol) in methanol (50 mL) was purged with nitrogen prior to the addition of 10% Pd/C catalyst (0.12 g). The mixture was again purged with nitrogen and then purged with hydrogen from a balloon. The mixture was stirred under hydrogen overnight. Additional amount of 10% Pd/C catalyst (0.24 g) was added, and the mixture was stirred under hydrogen overnight. The reaction mixture was filtered through a pad of celite, and the filtrate was concentrated. The residue was subjected to silica gel chromatography eluted with 100% DCM to provide methyl 2-[(2-aminophenyl)thio]benzoate as a yellow oil that crystallized over time. MS (ES, M+H$^+$): 260.2

Step 3: Methyl 2-{[2-({[4-(acetylamino)phenyl]sulfonyl}amino)phenyl]thio}benzoate A solution of methyl 2-[(2-aminophenyl)thio]benzoate (0.444 g, 1.71 mmol) and 4-(acetylamino)benzenesulfonyl chloride (0.440 g, 1.88 mmol) in pyridine (1.6 mL) was stirred at room temperature for 1 hr. The reaction mixture was diluted with ethyl acetate and washed with 0.5 N HCl (×2), water (×2), half brine and brine. The organic layer was dried over sodium sulfate, filtered, and concentrated. The residue was purified by silica gel chromatography eluted with 1-5% MeOH in DCM to provide the title compound. MS (ES, M+H$^+$): 457.2. $^1$H NMR (400 MHz, CD$_3$OD) δ 7.92 (bd, J=8 Hz, 1H), 7.75 (bd, J=8 Hz, 1H), 7.55 (bd, J=9.2 Hz, 2H), 7.50-7.44 (m, 3H), 7.42 (bd, J=8 Hz, 1H), 7.18 (bt, J=7.6 Hz, 1H), 7.14 (bt, J=7.6 Hz, 1H), 7.05 (bt, J=8 Hz, 1H), 6.23 (bd, J=8 Hz, 1H), 3.95 (s, 3H), 2.14 (s, 3).

EXAMPLE 3

Methyl 4-({[2-(2,4-dichlorophenoxy)phenyl]amino}sulfonyl)phenylcarbamate

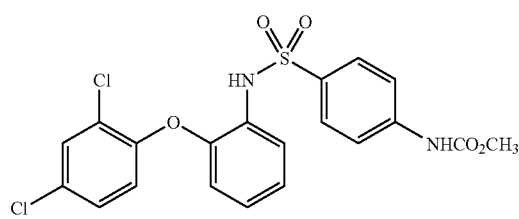

To a solution of 4-isocyanatobenzenesulfonyl chloride (0.20 g, 0.92 mmol) in pyridine (0.92 mL) at 0° C. was added methanol (38 μL, 0.92 mmol). The ice bath was removed after 5 min, and the reaction mixture was slowly warmed to room temperature. After 1.5 hrs of stirring, 2-(2,4-dichloro-phenoxy)aniline hydrochloride (0.27 g, 0.92 mmol) was added. After 1.5 hrs of stirring, the reaction mixture was diluted with ethyl acetate and washed with 0.5 N HCl (×2), water (×2), half brine and brine. The organic layer was dried over sodium sulfate, filtered, and concentrated. The residue was purified by silica gel chromatography eluted with 10-60% ethyl acetate in hexane to provide the title compound. MS (ES, M+H+): 467.0. $^1$H NMR (400 MHz, CD$_3$OD) δ 7.62 (m, 3H), 7.48 (d, J=2.4 Hz, 1H), 7.43 (dd, J=9.2 Hz, 2H), 7.09 (m, 3H), 6.58 (m, 1H), 6.37 (d, J=8.8 Hz, 1H), 3.76 (s, 3H).

EXAMPLE 4

N-[4-({[2-(2,4-dichlorophenoxy)phenyl]amino}sulfonyl)phenyl]pyrimidine-5-carboxamide

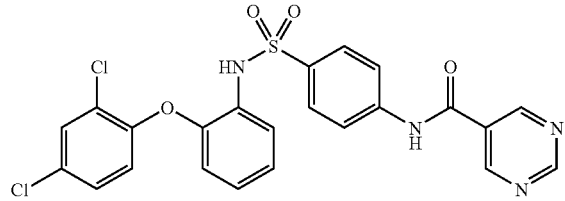

Step 1: N-[2-(2,4-dichlorophenoxy)phenyl]-4-nitrobenzenesulfonamide

A mixture of 4-nitrobenzenesulfonyl chloride (2.71 g, 12 mmol) and 2-(2,4-dichloro-phenoxy)aniline HCl (2.9 g, 10 mmol) were dissolved in pyridine (10 mL) at room temperature. After 1 hr the mixture was heated at 60° C. for 2 hour. The reaction mixture was concentrated under vacuum. The residue was diluted with EtOAc and washed sequentially with 1M aq. HCl and sat. aq. NaHCO$_3$ and the organic extract dried over MgSO$_4$, and the solvent removed in vacuo to afford the title compound as a solid. LCMS (ES MS, M+H$^+$ found: 439) and proton NMR (400 MHz, CDCl$_3$) δ 6.54-6.62 (m, 2H), 7.02-7.18 (m, 4H), 7.43 (d, J=2.5 Hz, 1H), 7.73 (dd, J=8.1 and 1.6 Hz, 1H), 7.94 (d, J=8.6 Hz, 2H), 8.21 (d, J=8.6 Hz, 2H).

Step 2: 4-amino-N-[2-(2,4-dichlorophenoxy)phenyl]benzenesulfonamide

To a solution of the compound of Step 1 (2.12 g) in methanol (50 mL) and CH$_2$Cl$_2$ (50 mL) was added a solution of sodium metabisulfite (2.52 g) in water (50 mL) at room temperature. After 3 hrs the methanol was evaporated in vacuo. The residue was partitioned between sat. aq. Na$_2$CO$_3$ and EtOAc, Dried over MgSO$_4$ and evaporated in vacuo. The resulting orange solid was absorbed onto silica gel (10 g) and purified by flash chromatography SiO$_2$, 0-50% EtOAc Hexanes gradient elution to afford the title compound as a yellow solid. C18H14Cl2N2O3S MH+ requires 409.0175 found 409.0162.

Step 3: N-[4-({[2-(2,4-dichlorophenoxy)phenyl]amino}sulfonyl)phenyl]pyrimidine-5-carboxamide To a solution of the compound of Step 2 (0.1 g, 0.244 mmol), pyrimidin-5-carboxylic acid (0.03 g, 0.244 mmol) HOAT (0.033 g, 0.244 mmol) and EDC (0.047 g, 0.244 mmol) in DMF (1 mL) at room temperature was added triethylamine (0.068 mL, 0.489 mmol). After 18 hr pyrimidin-5-carboxylic acid (0.03 g, 0.244 mmol) HOAT (0.033 g, 0.244 mmol), EDC (0.047 g, 0.244 mmol) and triethylamine (0.068 mL, 0.489 mmol) were added. The reaction mixture was stirred for a further 16 hr, diluted with DME (2 mL), treated with trifluoroacetic acid, and purified directly by reverse phase HPLC waters Prepak C-18 column eluting with 5-95% CH$_3$CN: water containing 0.1% TPA. The pure fractions were combined and lyophilized to afford the title compound. C23H16Cl2N4O4S MH+ requires 515.0342 found 515.0349. Proton NMR (400 MHz, CDCl$_3$) δ 6.53 (d, J=8.8 Hz, 1H), 6.62 (d, J=8.2 Hz), 7.00-7.10 (m, 3H), 7.14 (t, J=7.8 Hz, 1H), 7.41 (d, J=2.5 Hz, 1H), 7.64(d, J=8.6 Hz, 2H), 7.70-7.80 (m, 3H), 8.03(s, 1H), 9.28 (s, 2H), 9.43 (s, 1H).

EXAMPLE 5

N-[4-({[2-(2,4-dichlorophenoxy)phenyl]amino}sulfonyl)phenyl]-2,2,2-trifluoroacetamide

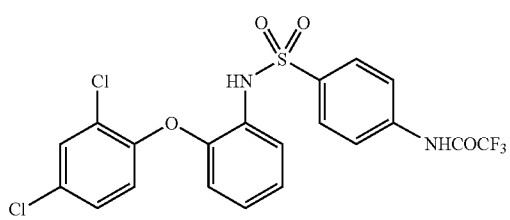

To a solution of 4-amino-N-[2-(2,4-dichlorophenoxy)phenyl]benzenesulfonamide (0.1 g, 0.244 mmol), in pyridine (1 mL) at 0 C was added trifluoroacetic anhydride (0.053 mL, 0.375 mmol). The reaction mixture was stirred for 2 hr at room temperature, concentrated in vacuo and the residue diluted with DMF (3 mL), treated with trifluoroacetic acid (2 drops) and purified directly by reverse phase HPLC waters Prepak C-18 column eluting with 5-95% CH$_3$CN: water containing 0.1% TFA. The pure fractions were combined and lyophilized to afford the title compound. C20H13Cl2F3N2O4S MH+ requires 504.9998 found 505.0003. Proton NMR (400 MHz, CDCl3) δ 6.53 (d, J=8.8 Hz, 1H), 6.60 (d, J=1.2 and 8.2 Hz), 7.00-7.10 (m, 3H), 7.12 (t, J=7.2 Hz, 1H), 7.41 (d, J=2.5 Hz, 1H), 7.58 (d, J=8.8 Hz, 2H), 7.73 (dd, J=1.4 and 8 Hz), 7.77 (d, J=8.8 Hz, 2H), 7.95 (s, 1H).

EXAMPLE 6

N-[2-chloro-4-({[2-(2,4-dichlorophenoxy)phenyl]amino}sulfonyl)phenyl]acetamide

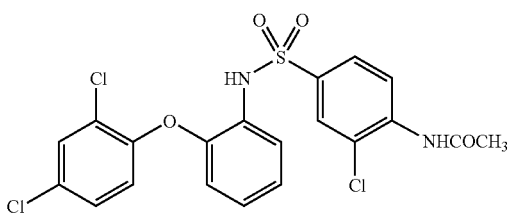

The title compound was prepared in a manner analogous to that in Reference Example 3. MS (ES, M+H$^+$): 485.0 $^1$H NMR (400 MHz, CD$_3$OD) δ 8.01 (d, J=8.8 Hz, 1H), 7.74 (d, J=2 Hz, 1H), 7.62 (m, 1H), 7.58 (dd, J=8.8, 2.4 Hz, 1H), 7.47 (d, J=2.8 Hz, 1H), 7.14-7.10 (m, 3H), 6.59 (m, 1H), 6.41 (d, J=8.8 Hz, 1H), 2.23 (s, 3H).

EXAMPLE 7

N-(2-benzoylphenyl)-4-({[(3-piperidin-1-ylpropyl)amino]carbonyl}amino)benzenesulfonamide

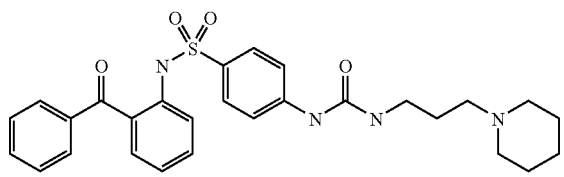

Triphosgene (28 mg, 1/3 equiv) was dissolved in 1 mL of THF and the solution cooled to 0° C. A solution of 4-amino-N-(2-benzoylphenyl)benzenesulfonamide (100 mg) in 3 mL of THF and 0.15 mL of triethylamine was added therto, and the reaction mixture was warmed to rt and stirred for 30 minutes. A solution of 3-(piperidin-1-yl)propan-1-amine (60 mg, 1.5 equiv) in 3 mL of THF and 0.15 mL of triethylamine was added thereto and the reaction mixture was left stirring overnight. The reaction was quenched with water and diluted with EtOAc. The organic layer was washed once each with water and brine, dried over sodium sulfate, filtered, and concentrated in vacuo. The title product was obtained as the TFA salt following reverse phase chromatography (5% to 95% acetonitrile/water/0.1% TFA). ESMS, M+H+ found: 521.2.

EXAMPLE 8

N-{2-[(5-fluoropyridin-2-yl)carbonyl]phenyl}-4-({[(benzyl)amino]carbonyl}amino)benzenesulfonamide

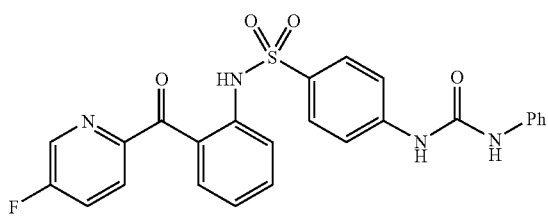

The title compound was prepared following the general procedure described in Example 10. MS 505.

EXAMPLE 9

Tetrahydrofuran-2-ylmethyl 4-{[(2-benzoylphenyl)amino]sulfonyl}phenylcarbamate

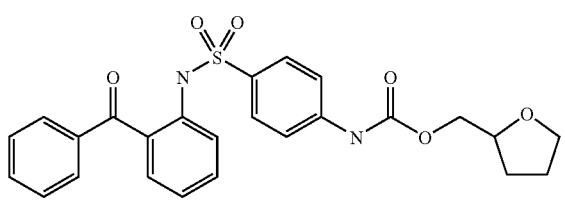

Triphosgene (28 mg, 1/3 equiv) was dissolved in 1 mL of THF and the solution cooled to 0° C. A solution of 4-amino-N-(2-benzoylphenyl)benzenesulfonamide (100 mg) in 3 mL of THF and 0.15 mL of triethylamine was added therto, and the reaction mixture was warmed to rt and stirred for 30 minutes. A solution of tetrahydrofurfuryl alcohol (44 mg, 1.5 equiv) in 3 mL of THF and 0.15 mL of triethylamine was added thereto and the reaction mixture was left stirring overnight. The reaction was quenched with water and diluted with EtOAc. The organic layer was washed once each with water and brine, dried over sodium sulfate, filtered, and concentrated in vacuo. The title product was obtained following flash chromatography (10% to 95% EtOAc/hexanes). ESMS, M+H+ found: 481.8.

EXAMPLE 10

4-(3-Benzyl-2-oxoimidazolidin-1-yl)-N-{2-[(5-fluoropyridin-2-yl)carbonyl]phenyl}benzenesulfonamide

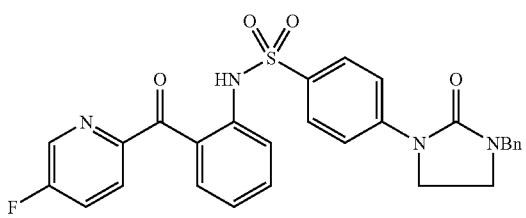

Step 1. 1-phenylimidazolidin-2-one

Triphosgene (3.6 g, 12.2 mmol) was dissolved in 40 mL of THF and cooled to 0° C. To the resulting solution was added 5 g (36.7 mmol) of N-phenylethylenediamine dissolved in 65 mL of THF and 7.7 mL (1.5 equiv) of triethylamine over 30 min. White solid immediately crashed out. The reaction was complete after 5 min. as indicated by LC/MS The reaction wasuenched with water and diluted with EtOAc. The organic layer was washed with water (1×100 mL) and brine (1×100 mL), dried over sodium sulfate, filtered, and concentrated in vacuo to provide the crude title compound, which was used without further purification (LC/MS, found: 163.2)

Step 2. 4-(2-oxoimidazolidin-1-yl)benzenesulfonyl chloride

To 1.5 mL (23.1 mmol) of chlorosulfonic acid in 3 mL of carbon tetrachloride at 0° C. was added slowly 500 mg (3.1 mmol) of the compound of Step 1. The reaction was almost completed after 2 h at 0° C. The reaction mixture was poured into ice water slowly, then filtered to collect the solids formed. The aqueous layer was extracted with chloroform (3×100 ml), and the combined organic layers were dried over sodium sulfate, filtered, concentrated in vacuo. The filtered solid and the crude material from the extraction were combined to provide the title compound (LC/MS found: 261.1)

Step 3. N-{2-[(5-fluoropyridin-2-yl)carbonyl]phenyl}-4-(2-oxoimidazolidin-1-yl)benzenesulfonamide To a solution of 100 mg (0.46 mmol) of (2-aminophenyl)(5-fluoropyridin-2-yl)-methanone and 180 mg (1.5 equiv) of the compound of Step 2 in 1 mL of CH2Cl2 was added 0.11 mL (1.38 mmol) of pyridine. The resulting reaction mixture was stirred overnight at room temperature and then was concentrated in vacuo and purified via reverse phase chromatography (5% to 95% acetonitrile/water/0.1% trifluoroacetic acid) to provide the title compound as the TFA salt (LC/MS found: 441.2).

Step 4. 4-(3-benzyl-2-oxoimidazohdin-1-yl)-N-{2-[(5-fluoropyridin-2-yl)carbonyl]phenyl}benzenesulfonamide To a solution of 50 mg (0.114 mmol) of the compound of Step 3 in 1 mL of THF was added 0.284 mL (0.284 mmol) of 2.0 M LiHMDS solution in THF at room temperature and the resulting solution was stirred for 15 minutes. To the solution was then added 19 mg (0.114 mmol) of benzyl bromide and stirred overnight at rt. The reaction mixture was quenched with water, diluted with EtOAc (~100 mL), and the organic layer was collected, dried over sodium sulfate, filtered, and concentrated in vacuo. Preparative TLC on 1 mm plate (50% EtOAc/hexanes) gave ~30 mg of impure material. Reverse phase chromatography (5% to 95% AcCN/H2O/0.1% TFA) and followed up by another preparative TLC on 0.5 mm plate (60% EtOAc/hexanes/trace triethyl amine) gave the title compound (LC/MS found: 531.2)

The following cyclic ureas were prepared according to the general procedure described in Example 10:

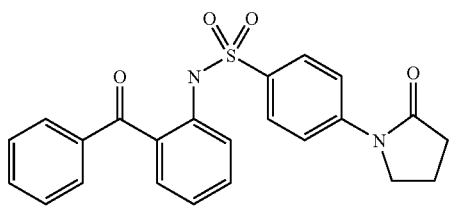

| Ex. | Ar | Y | R | MS |
|---|---|---|---|---|
| 11 | 5-F-2-pyridyl | 0 | 2-tetrahydrofuraylmethyl | 525 |
| 12 | Phenyl | 0 | H | |
| 13 | 5-F-2-pyridyl | 0 | CH$_2$CH(CH$_3$)$_2$ | 497 |
| 14 | 5-F-2-pyridyl | 0 | CH$_3$ | 455 |
| 15 | 5-F-2-pyridyl | 0 | H | 441 |
| 16 | 5-F-2-pyridyl | 0 | CH(CH$_3$)$_2$ | 483 |
| 17 | phenyl | 1 | H | |
| 18 | 5-F-2-pyridyl | 1 | H | |
| 19 | 5-F-2-pyridyl | 1 | benzyl | 545 |
| 20 | 5-F-2-pyridyl | 1 | 2-tetrahydrofuranylmethyl | 520 |
| 21 | 5-F-2-pyridyl | 1 | CH$_3$ | 469 |

EXAMPLE 22

N-(2-benzoylphenyl)-4-(2-oxopyrrolidin-1-yl)benzenesulfonamide

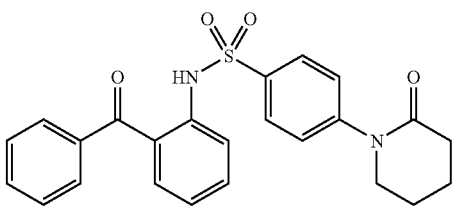

Step 1. N-(4-{[(2-benzoylphenyl)amino]sulfonyl}phenyl)-4-chlorobutanamide.

A solution of 474 mg (2.84 mmol) of 4-bromo-butanoic acid in 6 mL of 5:1 HMPA/acetonitrile was cooled to 0 deg and thionyl chloride (0.207 mL, 2.84 mmol) was added. The reaction mixture was warmed to room temperature, and transferred to a flask containing 250 mg (0.709 mmol) of neat 4-amino-N-(2-benzoylphenyl)benzenesulfonamide. The solution was allowed to stir overnight. The reaction was quenched w/saturated sodium bicarbonate and diluted with EtOAc (~100 mL), washed with water (3×20 mL) and brine (1×20 mL), dried over sodium sulfate, filtered, and concentrated in vacuo. The residue was purified via flash chromatography (15% to 75% EtOAc/hexanes)to provide the title compound. LC/MS (ES MS, M+H$^+$ found: 457).

Step 2. N-(2-benzoylphenyl)-4-(2-oxopyrrolidin-1-yl)benzenesulfonamide

The above compound (180 mg, 0.393 mmol) was dissolved in 3 mL of THF and the solution cooled to 0° C. NaH (24 mg, 60% dispersion in mineral oil, 0.590 mmol) was added and the reaction mixture warmed to rt and left stirring overnight. The reaction was quenched with water and diluted with EtOAc (~100 mL), washed with brine (1×20 mL), dried over sodium sulfate, filtered, and concentrated in vacuo. The residue was urified via flash chromatography (10% to 90% EtOAc/hexanes) to provide the title compound. LC/MS (ES MS, M+H$^+$ found: 421.2).

EXAMPLE 23

N-(2-benzoylphenyl)-4-(2-oxopiperidin-1-yl)benzenesulfonamide

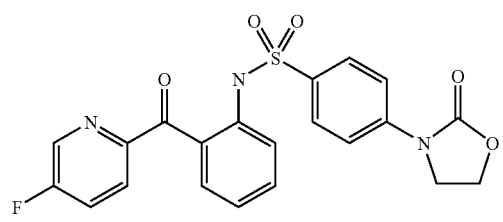

The title compound was prepared analogously as described in Example 22.

EXAMPLE 24

N-{2-[(5-Fluoropyridin-2-yl)carbonyl]phenyl}-4-(2-oxo-1,3-oxazolidin-3-yl)benzenesulfonamide Under N$_2$, a solution of N-(2-hydroxyethyl)aniline (500 mg, 3.65 mmol) and triethylamine (1 mL, 7.29 mmol) in THF (2 mL) was added slowly to a solution of triphosgene (360 mg, 1.21 mmol) in THF (2 mL) at 0° C. The reaction mixture was stirred at 0° C. for one hour. The reaction was then quenched with a saturated solution of sodium bicarbonate (4 mL) and extracted with methylene chloride (3×4 mL). The organic extracts were dried over sodium sulfate and concentrated. Silica gel chromatography (5%-35% EtOAc/CH$_2$Cl$_2$) gave 3-phenyl-1,3-oxazolidin-2-one. LCMS (ES) m/z 164.2 (M+H)$^+$.

Under N$_2$, chlorosulfonic acid (1.5 g, 12.87 mmol) was diluted in CCl$_4$ (2 mL) and cooled to 0° C. Then 3-phenyl-1,3-oxazolidin-2-one (280 mg, 1.72 mmol) was diluted in CCl$_4$ (2 mL) and added slowly to the reaction mixture. The reaction mixture was stirred for two hours at 0° C. The reaction was then slowly quenched with ice water (4 mL) and extracted with CCl$_4$ (3×4 mL). The organic extracts were dried over sodium sulfate and concentrated to give 4-(2-oxo-1,3-oxazo-lidin-3-yl)-benzenesulfonyl chloride which was used without purification.

Under $N_2$, (2-aminophenyl)(5-flurorpyridin-2-yl)methanone (87 mg, 0.401 mmol) was diluted in pyridine (2 mL) and then 4-(2-oxo-1,3-oxazolidin-3-yl)benzenesulfonyl chloride (70 mg, 0.267 mmol) was added. The reaction mixture was stirred at room temperature overnight, concentrated, and purified by reverse phase chromatography to yield the title compound. LCMS (ES) m/z 442.1 (M+H)+.

EXAMPLE 25

N-{2-[(5-Fluoropyridin-2-yl)carbonyl]phenyl}-4-(5-benzyl-2-oxo-1,3-oxazolidin-3-yl)benzenesulfonamide

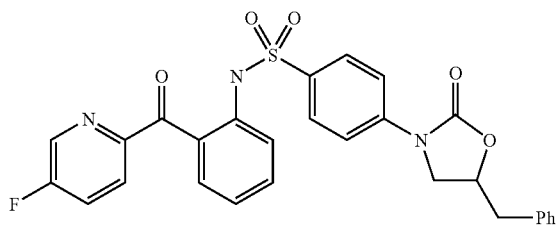

In an oven dried flask and under a nitrogen atmosphere, (2,3-epoxypropyl)benzene (145 mg, 1.077 mmol) was diluted in THF (1 mL) and cooled to −78° C. Then boron trifluoride diethyl etherate (150 uL, 1.185 mmol) was added, and the reaction was allowed to stir at −78° C. In a separate oven dried flask and under a nitrogen atmosphere, 4-amino-N-{2-[(5-fluoropyridin-2-yl)carbonyl]-phenyl}benzenesulfonanide (400 mg, 1.077 mmol) was diluted in THF (6 mL) and cooled to −78° C. Then LiHMDS (2 mL, 2.154 mmol) was added. After 5 minutes of stirring at −78° C. the LiHMDS reaction was warmed to 0° C. and allowed to spin for 30 minutes. It was then re-cooled to −78° C. and was added to the epoxide reaction via a cannula. The reaction then stirred at −78° C. for 2 hours. It was warmed to 0° C. and allowed to spin for an additional hour. The reaction was then quenched with water (15 mL) and extracted with methylene chloride (3×20 mL). The organic extracts were dried over sodium sulfate and concentrated. Reverse phase chromatography (5%-95% AcCN/H₂O) gave N-{2-[(5-fluoro-pyridin-2-yl)carbonyl]phenyl}-4-[(2-hydroxy-3-phenylpropyl)amino]benzenesulfonamide (110 mg, 20%). LCMS (ES) m/z 506.3 (M+H)+.

Under nitrogen atmosphere, a solution of the above compound (44 mg, 0.087 mmol) and triethylamine (24 uL, 0.174 mmol) in THF (1 mL) was added slowly to a solution of triphosgene (9 mg, 0.029 mmol) in THF (500 uL) at 0° C. The reaction mixture stirred at 0° C. for one hour. The reaction was then quenched with a saturated solution of sodium bicarbonate (2 mL) and extracted with methylene chloride (3×4 mL). The organic extracts were dried over sodium sulfate and concentrated. Reverse phase chromatography (5%-95% AcCN/H2O) gave 4-(5-benzyl-2-oxo-1,3-oxazolidin-3-yl)-N-{2-[(5-fluoro-pyridin-2-yl)carbonyl] phenyl}benzenesulfonamide (10 mg, 22%). LCMS (ES) m/z 532.3 (M+H)+.

EXAMPLE 26

N-[5-({[2-(2,4-dichlorophenoxy)phenyl]amino}sulfonyl)pyridin-2-yl]acetamide

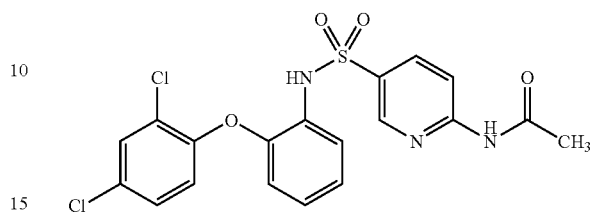

2-(2,4-Dichlorophenoxy)aniline HCl (1.14 g, 3.94 mmol) and 5-bromo-6-chloropyridine-3-sulfonyl chloride (1.26 g, 4.33 mmol) were dissolved in pyridine (4 mL) and allowed to stir at ambient temperature for 1 hour. The reaction mixture was then diluted with 100 mL of ethyl acetate, 80 mL of 0.5 M HCl. The organic layer was washed successively with 100 mL of 0.5 M HCl, twice with 100 mL of water, 100 mL of half-saturated brine and finally 100 mL of brine. Drying of the organic layer over sodium sulfate was followed by filtration and solvent removal under reduced pressure. The resulting residue was purified by silica gel chromatography (linear gradient 60-100% DCM in hexanes) to yield 5-bromo-6-chloro-N-[2-(2,4-dichlorophenoxy)phenyl]pyridine-3-sulfonamide, giving proton NMR and mass spectral data consistent with theory.

To a stirred, dry DMSO solution (5 mL) of the above compound (0.350 g, 0.688 mmol) was added sodium azide (89.0 mg, 1.38 mmol). The solution was allowed to stir at ambient temperature under an inert atmosphere for >16 h. The reaction mixture was then diluted with 100 mL of water and 100 mL of diethyl ether. The organic layer was washed successively with water, half-saturated brine and brine. Drying of the organic layer over sodium sulfate was followed by filtration and solvent removal under reduced pressure to provide 6-azido-5-bromo-N-[2-(2,4-dichlorophenoxy)phenyl] pyridine-3-sulfonamide of sufficient purity to obviate further purification. Proton NMR and mass spectral data were found to be consistent with theory.

The above compound (0.300 g, 0.582 mmol) was dissolved in 5 mL of a 25% acetic acid in EtOH solution. Zinc dust (0.952 g, 14.6 mmol) was then added. A reflux condenser was attached and the mixture was heated to 40° C. for 3 h. The mixture was then allowed to cool to ambient temperature before being diluted with water and ethyl acetate. The organic layer was washed successively with 5% sodium bicarbonate and brine. Drying of the organic layer over sodium sulfate was followed by filtration and solvent removal under reduced pressure. The resulting residue was purified by silica gel chromatography (linear gradient 1-6% MeOH in DCM) to yield 6-amino-N-[2-(2,4-dichlorophenoxy)phenyl]-pyridine-3-sulfonamide. Proton NMR and mass spectral data were found to be consistent with theory.

The above compound (70.0 mg, 0.171 mmol) was dissolved in DCM and cooled to 0° C. Pyridine (16.0 mg, 0.205 mmol) and BOC anhydride (37.0 mg, 0.171 mmol) were then added. Stirring was continued and the ice bath was allowed to melt overnight. The next day, acetyl chloride (19.5 mg, 0.257 mmol) was added and after 5 h the reaction was judged complete by LCMS. Solvent was removed under reduced pressure and the residue was purified by silica gel chromatography (linear gradient 0.5-2.5% MeOH in DCM) to yield tert-butyl {[6-(acetylamino)pyridin-3-yl]sulfonyl}[2-(2,4- dichlorophenoxy)phenyl]carbamate. Proton NMR and mass spectral data were found to be consistent with theory.

The above compound (70.0 mg, 0.127 mmol) was dissolved in ethyl acetate (5 mL) prior to cooling to 0° C. in an ice bath. Anhydrous hydrogen chloride was bubbled through this solution for 3 minutes, after which time the reaction was allowed to sit an additional 60 min at 0° C. Dry nitrogen was then bubbled through the solution for 30 minutes. Solvent was removed. The residue was then dissolved in DCM, followed by concentration under reduced pressure (repeated twice) to yield the title compound as its hydrochloride salt in 91% purity; the remaining 9% was determined to be 6-amino-N-[2-(2,4-dichlorophenoxy)phenyl]pyridine-3-sulfonamide. Proton NMR and mass spectral data for the major component were found to be consistent with theory. LCMS (ES, M+H$^+$): 452. HRMS (FT/ICR, M+H$^+$) 452.0234 (Theory: 452.0233). $^1$H NMR (CD$_3$OD, 400 MHz) δ 8.50 (d, J=2.0 Hz, 1H), 8.20 (dd, J=9.2, 2.4 Hz, 1H), 7.86 (d, J=8.8 Hz, 1H), 7.62 (m, 1H), 7.49 (d, J=2.4 Hz, 1H), 7.17 (m, 3H), 6.63 (m, 1H), 6.57 (d, J=8.8 Hz, 1H), 2.24 (s, 3H).

EXAMPLE 27

Tetrahydrofuran-2-ylmethyl 6-{[([(5-fluoropyridin-2-yl)carbonyl]phenyl)amino]sulfonyl}pyridyl-3-carbamate (Enantiomers A and B)

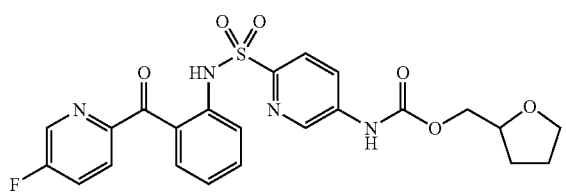

The title compound was prepared in a manner analogous to that described in Examples 12 to provide a racemic mixture, which was separated into the individual enantiomers using conventional chiral HPLC methodology.

Compounds in Table 1 were prepared from 4-(acetylamino)benzenesulfonyl chloride and the appropriate (2-aminophenyl)(aryl)methanone or 2-aryloxyaniline. The ketones may be prepared analogously as described in Reference Example 2, and the ethers analogously as described in Reference Example 3. N-oxides may be obtained using conventional oxidation reagent such as mCPBA.

TABLE 1

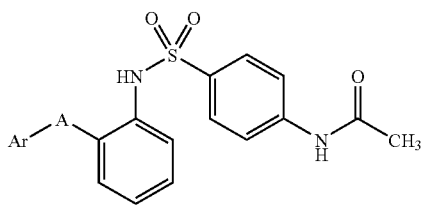

| Ex. | A | Ar | MS |
|---|---|---|---|
| 28 | C(O) | 1,2,3,4-tetrahydro-8-quinolinyl | |
| 29 | O | 2-CH$_3$-3-pyridyl | 398 |
| 30 | O | 2-Cl-3-pyridyl | 418 |
| 31 | O | 2-CN-3-pyridyl | 409 |
| 32 | C(O) | 2-pyridyl | 396 |
| 33 | C(O) | 3-pyridyl | 396 |
| 34 | O | 3-pyridyl | 384 |
| 35 | C(O) | 3-pyridyl-N-oxide | 412 |

TABLE 1-continued

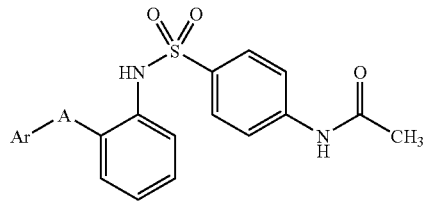

| Ex. | A | Ar | MS |
|---|---|---|---|
| 36 | C(O) | 4-pyridyl | 396 |
| 37 | C(O) | 4-pyridyl-N-oxide | 412 |
| 38 | O | 5-Br-3-pyridyl | 463 |
| 39 | O | 5-Cl-2-pyridyl | 419 |
| 40 | C(O) | 5-Cl-2-pyridyl | 430 |
| 41 | O | 5-Cl-3-pyridyl | 419 |
| 42 | C(O) | 5-F-2-pyridyl | 414 |
| 43 | O | 6-Cl-3-pyridyl | 418 |
| 44 | C(O) | 6-F-3-pyridyl | 414 |
| 45 | O | 6-F-3-pyridyl | 402 |
| 46 | C(O) | 8-quinolinyl | |

Compounds in Table 2 were prepared following the general procedure of Example 7 using the appropriate amines, which are either commercially available or may be derivatized from commercially available material by well-known methods.

TABLE 2

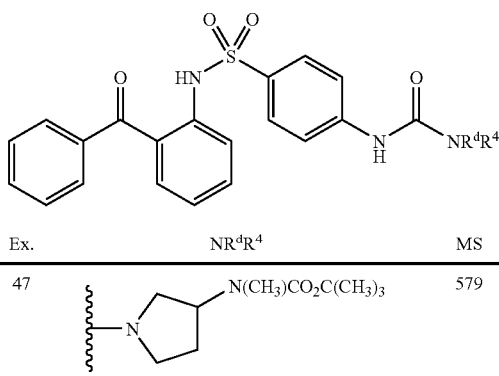

| Ex. | NR$^d$R$^4$ | MS |
|---|---|---|
| 47 |  N(CH$_3$)CO$_2$C(CH$_3$)$_3$ | 579 |
| 48 | 1-piperazinyl | 465 |
| 49 | 3-(2-pyridyl)-1-pyrrolidinyl | 527 |
| 50 | 3-(BOC-amino-1-piperidinyl | 579 |
| 51 | 3-amino-1-piperidinyl | 516 |
| 52 | 3-fluoro-1-piperidinyl | 482 |
| 53 | 3-hydroxy-1-piperidinyl | 480 |
| 54 | 3-methoxy-1-piperidinyl | 493 |
| 55 | 3-methylamino-1-pyrrolidinyl | 479 |
| 56 | 4-acetyl-1-piperazinyl | 507 |
| 57 | 4-BOC-1-piperazinyl | 565 |
| 58 | 4-methyl-1-piperazinyl | 479 |
| 59 | 4-morpholinyl | 466 |
| 60 | 4-oxo-1-piperidinyl | 478 |
| 61 | 4-phenyl-1-piperazinyl | 541 |

Compounds of Tables 3a, 3b, 4, and 5 were prepared following the general procedures for amide, carbamate and urea formation described in Reference Example 3 and Examples presented above. The acid precursors (R$_4$CO$_2$H or acylating equivalents thereof) are commercially available, or known in the literature, or may be prepared from known or commercially available starting material using standard organic reactions.

TABLE 3a
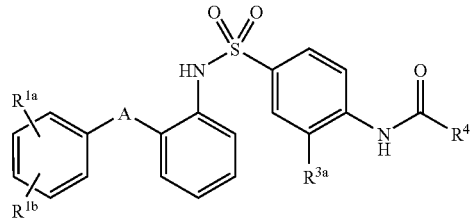
| Ex. | A | R¹ᵃ/R¹ᵇ | R³ᵃ | R⁴ | MS |
|---|---|---|---|---|---|
| 62 | C(O) | H/H | H | —(CH₂)₂—C(O)—N-piperidine-OH | 536 |
| 63 | C(O) | H/H | H | —(CH₂)₃—N-piperidine | 506 |
| 64 | C(O) | H/H | H | —(CH₂)₃—N-piperidine-OH | 522 |
| 65 | C(O) | H/H | H | —(CH₂)₂—C(O)—N-piperidine-3-OH | 536 |
| 66 | O | 2,4-diCl | H | —(CH₂)₃—N-piperidine | 563 |
| 67 | C(O) | H/H | H | —(CH₂)₂—N-piperidine | 492 |
| 68 | C(O) | H/H | H | —(CH₂)₂—N-pyrrolidine | 592 |
| 69 | C(O) | H/H | H | —(CH₂)₂—C(O)—N-piperidine-3-F | 538 |
| 70 | C(O) | H/H | H | —(CH₂)₂—C(O)—N-pyrrolidine | 506 |
| 71 | C(O) | H/H | H | —(CH₂)₂—C(O)—N-piperidin-4-one | 534 |
| 72 | C(O) | H/H | H | —(CH₂)₃—N-piperidine-3-F | 524 |

TABLE 3a-continued

| Ex. | A | $R^{1a}/R^{1b}$ | $R^{3a}$ | $R^4$ | MS |
|---|---|---|---|---|---|
| 73 | C(O) | H/H | H | —(CH$_2$)$_2$—C(O)—N(piperidine) | 520 |
| 74 | C(O) | H/H | H | —(CH$_2$)$_2$—N(piperidine-4-OH) | 508 |
| 75 | C(O) | H/H | H | —(CH$_2$)$_2$—C(O)—N(3,3-difluoropiperidine) | 556 |
| 76 | C(O) | H/H | H | —(CH$_2$)$_2$—N(3-fluoropiperidine) racemic mixture and isomers A & B | 510 |
| 77 | C(O) | H/H | H | —(CH$_2$)$_2$—N(3-hydroxypiperidine) | 508 |
| 78 | C(O) | H/H | H | —(CH$_2$)$_2$—C(O)—N(morpholine) | 522 |
| 79 | C(O) | H/H | H | —(CH$_2$)$_3$—N(morpholine) | 508 |
| 80 | C(O) | H/H | H | —(CH$_2$)$_2$—N(4-fluoropiperidine) | 510 |
| 81 | C(O) | H/H | H | —(CH$_2$)$_2$—N(3,3-difluoropiperidine) | 528 |
| 82 | C(O) | H/H | H | —(CH$_2$)$_3$—N(4,4-difluoropiperidine) | 542 |

TABLE 3a-continued
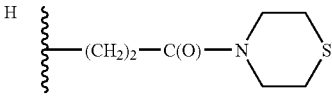
| Ex. | A | $R^{1a}/R^{1b}$ | $R^{3a}$ | $R^4$ | MS |
|---|---|---|---|---|---|
| 83 | C(O) | H/H | H | 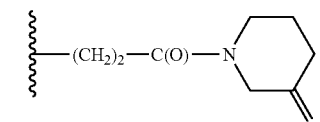 | 570 |
| 84 | C(O) | H/H | H | 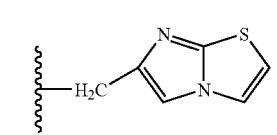 | 534 |
| 85 | C(O) | H/H | H | 4-methyl-2-morpholinyl | 480 |
| 86 | C(O) | H/H | H | 5-cyclopropyl-3-isoxazolyl | 488 |
| 87 | C(O) | H/H | H | 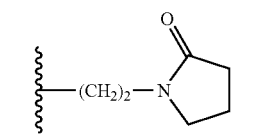 | 517 |
| 88 | C(O) | H/H | H | 5-methyl-3-isoxazolyl | 462 |
| 89 | C(O) | H/H | H | 3-methoxy-5-isoxazolyl | 478 |
| 90 | C(O) | H/H | H | 2-tetrahydrofuranylmethyl | 465 |
| 91 | C(O) | H/H | H | 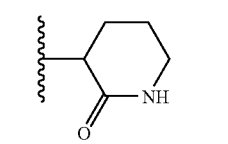 | 492 |
| 92 | C(O) | H/H | H | 3-phenyl-5-isoxazolyl | 524 |
| 93 | C(O) | H/H | H | 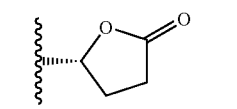 | 478 |
| 94 | C(O) | H/H | H | 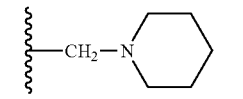 | 465 |
| 95 | C(O) | H/H | H | 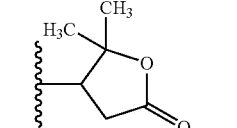 | 478 |
| 96 | C(O) | H/H | H |  | 493 |

TABLE 3a-continued
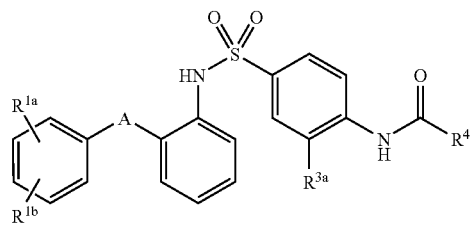
| Ex. | A | R¹ᵃ/R¹ᵇ | R³ᵃ | R⁴ | MS |
|---|---|---|---|---|---|
| 97 | C(O) | H/H | H | 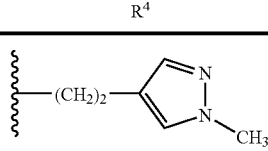 | 489 |
| 98 | C(O) | H/H | H | 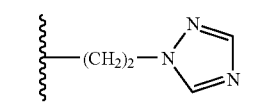 | 476 |
| 99 | C(O) | H/H | H | 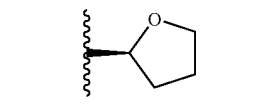 | 451 |
| 100 | C(O) | H/H | H | 4-tetrahydropyranylmethyl | 479 |
| 101 | C(O) | H/H | H | 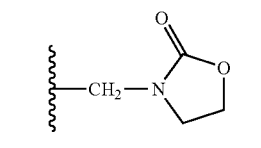 | 480 |
| 102 | C(O) | H/H | H | 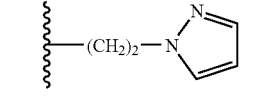 | 475 |
| 103 | C(O) | H/H | H | 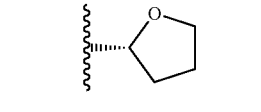 | 451 |
| 104 | C(O) | H/H | H | 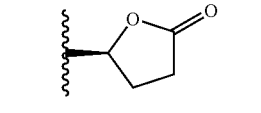 | 465 |
| 105 | C(O) | H/H | H | 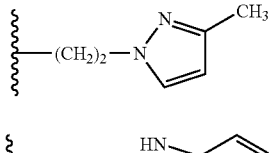 | 489 |
| 106 | C(O) | H/H | H | 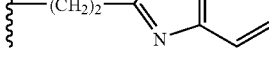 | 525 |
| 107 | C(O) | H/H | H | 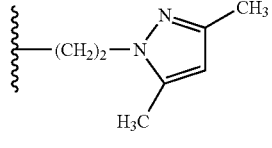 | 503 |

TABLE 3a-continued

| Ex. | A | R¹ᵃ/R¹ᵇ | R³ᵃ | R⁴ | MS |
|---|---|---|---|---|---|
| 108 | C(O) | H/H | H | -CH₂-(1H-benzimidazol-2-yl) | 511 |
| 109 | C(O) | H/H | H | benzo[d]isoxazol-3-yl | 498 |
| 110 | C(O) | H/H | H | -(CH₂)₂-(benzothiazol-2-yl) | 542 |
| 111 | C(O) | H/H | H | 3-tetrahydrofuranyl | 451 |
| 112 | C(O) | H/H | H | 2-tetrahydrofuranyl | 451 |
| 113 | C(O) | H/H | H | -(CH₂)-(5-oxopyrrolidin-2-yl) | 478 |
| 114 | C(O) | H/H | H | -(CH₂)₂-(benzimidazol-1-yl) | 525 |
| 115 | C(O) | H/H | H | -CH₂-(2,4-dioxoimidazolidin-5-yl) | 493 |
| 116 | C(O) | H/H | H | -CH₂-(imidazol-1-yl) | 461 |
| 117 | C(O) | H/H | H | 2-indolyl | 496 |
| 118 | C(O) | H/H | H | -(2-oxopyrrolidin-4-yl) | 464 |
| 119 | C(O) | H/H | H | 4-tetrahydropyranyl | 465 |
| 120 | C(O) | H/H | H | -CH₂-(1,2,4-triazol-1-yl) | 462 |

TABLE 3a-continued

| Ex. | A | R¹ᵃ/R¹ᵇ | R³ᵃ | R⁴ | MS |
|---|---|---|---|---|---|
| 121 | C(O) | H/H | H | 5-oxopyrrolidin-2-yl | 464 |
| 122 | O | 2,4-diCl | H | 1-(NHC(O)CF₃)cyclopropyl | 589 |
| 123 | C(O) | H/H | H | 2,2-dimethyltetrahydropyran-4-yl | 493 |
| 124 | C(O) | H/H | H | —(CH₂)₂CF₃ | 477 |
| 125 | C(O) | H/H | H | —(CH₂)₂cyclohexyl | 491 |
| 126 | C(O) | H/H | H | —(CH₂)₂—CO₂CH₃ | 467 |
| 127 | C(O) | H/H | H | —(CH₂)₂NH₂ | 424 |
| 128 | C(O) | H/H | H | —(CH₂)₂NHC(O)CH₃ | 466 |
| 129 | C(O) | H/H | H | —(CH₂)₂—NH—CO₂C(CH₃)₃ | 524 |
| 130 | C(O) | H/H | H | —(CH₂)₂—OCH₃ | 439 |
| 131 | C(O) | H/H | H | —(CH₂)₂Ph | 485 |
| 132 | C(O) | H/H | H | —(CH₂)₃Cl | 457 |
| 133 | C(O) | H/H | H | —(CH₂)₃—OCH₃ | 453 |
| 134 | C(O) | H/H | H | —(CH₂)₄Cl | 471 |
| 135 | C(O) | H/H | H | 2-pyrazinyl | 459 |
| 136 | C(O) | H/H | H | 2-pyridyl | 458 |
| 137 | C(O) | H/H | H | 3-pyridyl | 458 |
| 138 | C(O) | H/H | H | 4-pyridyl | 458 |
| 139 | C(O) | H/H | H | 5-isoxazolyl | 448 |
| 140 | C(O) | H/H | H | 5-pyrimidinyl | 459 |
| 141 | O | 2,4-diCl | H | 5-pyrimidinyl | 516 |
| 142 | C(O) | H/H | H | —CF₂CF₃ | 499 |
| 143 | O | 2,4-diCl | H | CF₃ | 506 |
| 144 | C(O) | H/H | H | —CH₂CF₃ | 463 |
| 145 | C(O) | 4-F | H | CH₃ | 413 |
| 146 | C(O) | 2,3-diF | H | CH₃ | 431 |
| 147 | C(O) | 2,4-diF | H | CH₃ | 431 |
| 148 | C(O) | 3-F | H | CH₃ | 413 |
| 149 | C(O) | 4—Cl | H | CH₃ | 429 |
| 150 | O | 4—Cl | H | CH₃ | 417 |
| 151 | C(O) | 3—Cl | H | CH₃ | 429 |
| 152 | O | 4-Br | H | CH₃ | 462 |
| 153 | O | 2,4-diF | H | CH₃ | 419 |
| 154 | O | 2—CN | H | CH₃ | 408 |
| 155 | O | 4-Cl-2-CN | H | CH₃ | 442 |
| 156 | O | 4-SCH₃ | H | CH₃ | 429 |
| 157 | O | 4—CN | H | CH₃ | 408 |
| 158 | C(O) | 2-F | H | CH₃ | 413 |
| 159 | O | 4-CF₃ | H | CH₃ | 450 |
| 160 | C(O) | 3,4-diF | H | CH₃ | 431 |
| 161 | C(O) | 4—CH₃ | H | CH₃ | 409 |
| 162 | C(O) | 3,5-diF | H | CH₃ | 431 |
| 163 | C(O) | 4-NO₂ | H | CH₃ | 440 |
| 164 | O | 2—Cl | H | CH₃ | 417 |
| 165 | O | 4-OCH₃ | H | CH₃ | 413 |
| 166 | O | H/H | H | CH₃ | 383 |
| 167 | O | 3-OCH₃ | H | CH₃ | 413 |
| 168 | O | 4-OCF₃ | H | CH₃ | 467 |
| 169 | O | 4-CH₂CH₂CN | H | CH₃ | 436 |

TABLE 3a-continued

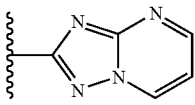

| Ex. | A | R$^{1a}$/R$^{1b}$ | R$^{3a}$ | R$^4$ | MS |
|---|---|---|---|---|---|
| 170 | O | 3-Cl | H | CH$_3$ | 417 |
| 171 | C(O) | 2,5-diF | H | CH$_3$ | 431 |
| 172 | C(O) | 4-CN | H | CH$_3$ | 420 |
| 173 | O | 3-CH$_2$CO$_2$H | H | CH$_3$ | 455 |
| 174 | C(O) | 4-OH | H | CH$_3$ | 411 |
| 175 | C(O) | 4-OCH$_3$ | H | CH$_3$ | 425 |
| 176 | NH | H/H | H | CH$_3$ | 382 |
| 177 | O | 1-imidazolyl | H | CH$_3$ | 449 |
| 178 | S | 2-CO$_2$CH$_3$ | H | CH$_3$ | 457 |
| 179 | O | 4-SO$_2$CH$_3$ | H | CH$_3$ | 461 |
| 180 | C(O) | H/H | H | cyclohexyl | 463 |
| 181 | C(O) | H/H | H | cyclopentyl | 449 |
| 182 | C(O) | H/H | H | cyclopropyl | 421 |
| 183 | C(O) | H/H | H | phenyl | 457 |
| 184 | C(O) | 4-CF$_3$ | H | CH$_3$ | 463 |
| 185 | O | 2,4-diCl | Cl | CH$_3$ | 486 |
| 186 | C(O) | H/H | Cl | CH$_3$ | 429 |
| 187 | C(O) | H/H | F | CH$_3$ | 413 |
| 188 | C(O) | H/H | H | 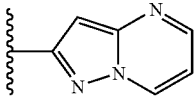 | 499 |
| 189 | C(O) | H/H | H | 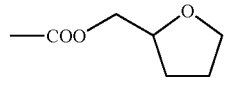 | 498 |
| 190 | C(O) | H/H | H | 2-methoxy-4-pyrimidinyl | 489 |
| 191 | C(O) | H/H | H | 2-chloro-4-pyrimidinyl | 493 |
| 192 | C(O) | H/H | H | 1-methyl-3-pyrazolyl | 461 |
| 193 | C(O) | H/H | H | —CO$_2$CH$_3$ | 439 |
| 194 | C(O) | H/H | H | —COCH$_2$CH(CH$_3$)$_2$ | 465 |
| 195 | C(O) | H/H | H | 2,4-dimethyl-5-thiazolyl | 492 |
| 196 | C(O) | H/H | H | 4-pyrimidinyl | 459 |
| 197 | C(O) | H/H | H | —CH$_2$OCH$_3$ | 425 |
| 198 | C(O) | H/H | H | —COO-tetrahydrofuranylmethyl | 509 |
| 199 | C(O) | H/H | H | 4-pyrazolyl | 447 |
| 200 | C(O) | H/H | H | 3-isoxazolyl | 448 |
| 201 | C(O) | H/H | H | 1,2,5-thiadiazol-3-yl | 465 |
| 202 | C(O) | H/H | H | 5-methyl-1,2,4-triazol-3-yl | 576 |
| 203 | C(O) | H/H | H | 1-methyl-4-pyrazolyl | 461 |
| 204 | C(O) | H/H | H | 5-thiazolyl | 464 |
| 205 | C(O) | 3-Br | H | —(CH$_2$)$_4$C≡CH | 540 |
| 206 | C(O) | H/H | H | 4-thiazolyl | 464 |
| 207 | C(O) | H/H | H | —C(O)CH$_3$ | 423 |
| 208 | C(O) | H/H | H | 1,2,3-triazolyl | 448 |
| 209 | C(O) | H/H | H | 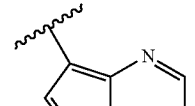 | 498 |
| 210 | C(O) | H/H | H | —C(O)NCH$_3$ | 438 |
| 211 | C(O) | H/H | H | 2-pyrimidinyl | 459 |

TABLE 3a-continued

| Ex. | A | R¹ᵃ/R¹ᵇ | R³ᵃ | R⁴ | MS |
|---|---|---|---|---|---|
| 212 | C(O) | H/H | H | —CH₂OH | 411 |
| 213 | C(O) | H/H | H | 5-oxazolyl | 448 |
| 214 | C(O) | H/H | H | 1,2,5-oxadizol-3-yl | 449 |
| 215 | C(O) | H/H | H | —C(O)N(CH₃)₂ | 452 |
| 216 | C(O) | 4-Br | H | —(CH₂)₄C≡CH | 540 |
| 217 | C(O) | H/H | H | 4-pyridazinyl | 459 |
| 218 | C(O) | H/H | H | 1,2,4-triazol-3-yl | 448 |
| 219 | C(O) | H/H | H | t-butyl | 439 |
| 220 | C(O) | H/H | H | 4-methyl-1-1,2,5-oxadiazol | 463 |
| 221 | C(O) | H/H | H | 3-methyl-4-pyrazolyl | 461 |
| 222 | C(O) | H/H | H | 3-indolyl | 496 |
| 223 | C(O) | H/H | H | 2-benzthienyl | 513 |
| 224 | C(O) | H/H | H | 4,5,6,7-tetrahydro-3-benzthienyl | 518 |
| 225 | C(O) | H/H | H | 3,6-dichloro-4-pyridazinyl | 528 |
| 226 | C(O) | H/H | H | 2-methyl-3-pyrazolyl | 461 |
| 227 | C(O) | H/H | H | 3,5-dimethylisoxazolyl | 476 |
| 228 | C(O) | H/H | H | 2-benzimidazolyl | 497 |

TABLE 3b

| Ex. | R⁴(R¹ᵃ = F, except specified) | MS |
|---|---|---|
| 229 | 7-trifluoromethyl-5-methyl-pyrazolo[1,5-a]pyrimidin-2-yl | 599 |
| 230 | pyrazolo[1,5-a]pyrimidin-2-yl | 517 |
| 231 | thieno[3,2-b]pyridin-6-yl | 533 |
| 232 | 5,7-dimethyl-pyrazolo[1,5-a]pyrimidin-2-yl | 545 |
| 233 | [1,2,4]triazolo[1,5-a]pyrimidin-2-yl | 518 |
| 234 | 4,5,6,7-tetrahydro-1H-indazol-3-yl | 520 |
| 235 | 4,5,6,7-tetrahydro-benzo[d]isoxazol-3-yl | 521 |
| 236 | pyrazolo[1,5-a]pyrimidin-3-yl | 517 |
| 237 | 1H-pyrrolo[2,3-b]pyridin-2-yl | 516 |
| 238 | 1,2,3-triazolyl | 467 |
| 239 | 1,2,4-triazolyl | 467 |
| 240 | 1,2,5-thiadiazolyl | 484 |
| 241 | 1,5-dimethyl-3-pyrazolyl | |
| 242 | 1-benzyl-5-methyl-3-pyrazolyl | 570 |
| 243 | 1-benzyl-5-methyl-3-pyrazolyl | 571 |
| 244 | 1-benzyloxy-1-trifluoromethylethyl | 602 |
| 245 | 1-methyl-3-pyrazolyl | 480 |
| 246 | 1-methyl-3-pyrazolyl* | 462 |

TABLE 3b-continued

| Ex. | R⁴ (R¹ᵃ = F, except specified) | MS |
|---|---|---|
| 247 | 1-phenyl-4-pyrazolyl | 542 |
| 248 | 2-(2-tetrahydrofuranyl)ethyl | 498 |
| 249 | 2-(dimethylamino)-4-pyrimidinyl | 521 |
| 250 | 2,4-dimethyl-5-thiazolyl | 511 |
| 251 | 2,5-dimethyl-3-pyrazolyl | 494 |
| 252 | 2-benzfuranyl | 516 |
| 253 | 2-chloro-4-pyrimidinyl | 512 |
| 254 | 2-ethyl-3-pyrazolyl | 660 |
| 255 | 2-methyl-4-thiazolyl | 497 |
| 256 | 2-methyl-5-(n-propyl)-3-pyrazolyl | 522 |
| 257 | 3-chloro-2-benzthienyl | 567 |
| 258 | 3-chloro-2-pyrimidinyl | 512 |
| 259 | 3-methoxy-5-isoxazolyl | 497 |
| 260 | 3-methoxy-5-isoxazolyl* | 479 |
| 261 | 3-phenyl-5-isoxazolyl | 543 |
| 262 | 5-(2-furanyl)-3-pyrazolyl | 532 |
| 263 | 5-(2-methylpropyl)-3-pyrazolyl | 522 |
| 264 | 5-(2-pyridyl)-3-pyrazolyl | 543 |
| 265 | 5-(3-pyridyl)-3-pyrazolyl | 543 |
| 266 | 5-(4-fluorophenyl)-3-pyrazolyl | 560 |
| 267 | 5-(4-pyridyl)-3-pyrazolyl | 543 |
| 268 | 5-(n-propyl)-3-isoxazolyl | 509 |
| 269 | 5-amino-1,2,4-triazolyl | 482 |
| 270 | 5-cyclopropyl-3-pyrazolyl | 508 |
| 271 | 5-ethyl-2-methyl-3-pyrazolyl | |
| 272 | 5-isopropyl-3-isoxazolyl | 509 |
| 273 | 5-isopropyl-3-pyrazolyl | 508 |
| 274 | 5-methyl-4-thiazolyl | 497 |
| 275 | 5-phenyl-2-furanyl | 542 |
| 276 | 5-phenyl-3-isoxazolyl | 543 |
| 277 | 5-phenyl-3-pyrazolyl | 542 |
| 278 | 5-trifluoromethyl-3-pyrazolyl | 534 |

*R¹ᵃ is hydrogen

TABLE 4

| Ex. | A | Ar | R⁴ | MS |
|---|---|---|---|---|
| 279 | C(O) | phenyl | —(CH₂)₃—piperidinyl | 522 |
| 280 | C(O) | phenyl | —CH₂—(tetrahydropyran-2-yl) | 495 |
| 281 | C(O) | phenyl | —CH₂—(4-benzylmorpholin-2-yl) | 586 |
| 282 | C(O) | phenyl | —(CH₂)₃—(3-fluoropiperidin-1-yl) | 540 |
| 283 | C(O) | phenyl | 2-tetrahydrofuranylmethyl | 481 |
| 284 | C(O) | phenyl | —(CH₂)₃—morpholinyl | 524 |
| 285 | C(O) | phenyl | —CH₂—(γ-butyrolactonyl) | 495 |
| 286 | C(O) | phenyl | —CH₂—(pyrrolidin-2-one-3-yl) | 494 |
| 287 | C(O) | phenyl | —CH₂—(pyrrolidin-2-one-5-yl) | 494 |
| 288 | O | 2,4-dichlorophenyl | —(CH₂)₂—piperidinyl | 565 |
| 289 | C(O) | phenyl | —(CH₂)₂—(tetrahydrofuran-2-yl) | 495 |
| 290 | C(O) | phenyl | —CH₂—(γ-butyrolactonyl) | 495 |
| 291 | C(O) | phenyl | —(CH₂)₃—(3,3-difluoropiperidin-1-yl) | 558 |
| 292 | C(O) | phenyl | —(CH₂)₂—morpholinyl | 510 |
| 293 | C(O) | phenyl | 3-tetrahydrofuranylmethyl | 481 |
| 294 | C(O) | phenyl | —CH₂—(3-t-butyl-oxazolidin-2-one-5-yl) | 552 |
| 295 | C(O) | phenyl | —CH₂—(1,3-dioxolan-2-one-4-yl) | 497 |
| 296 | O | 2,4-dichlorophenyl | —(CH₂)₂—morpholinyl | 567 |

TABLE 4-continued

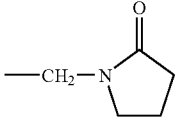

| Ex. | A | Ar | R⁴ | MS |
|---|---|---|---|---|
| 297 | C(O) | phenyl | 3-tetrahydrofuranylmethyl | 467 |
| 298 | C(O) | phenyl | 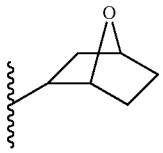 | 494 |
| 299 | C(O) | phenyl | 2-furanylmethyl | 477 |
| 300 | C(O) | phenyl | 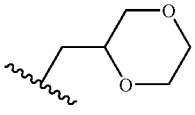 | 493 |
| 301 | C(O) | phenyl | —(CH$_2$)$_3$Ph | 515 |
| 302 | O | 2,4-dichloro-phenyl | 2-furanylmethyl | 534 |
| 303 | O | 2,4-dichloro-phenyl | methyl | 468 |
| 304 | C(O) | 2-pyridyl | 3-tetrahydrofuranylmethyl | 482 |
| 305 | C(O) | phenyl | 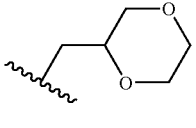 | 497 |
| 306 | C(O) | phenyl | (1-methyl-2-pyrrolidinyl)methyl | 493 |
| 307 | C(O) | phenyl | (1-methyl-5-oxo-2-pyrrolidinyl)methyl | 508 |
| 308 | C(O) | 5-fluoro-2-pyridyl | 2-tetrahydrofuranylmethyl Isomers A&B | 500 |
| 309 | C(O) | 2-pyridyl | 2-tetrahydrofuranylmethy Isomers A&B1 | 482 |
| 310 | C(O) | 5-chloro-2-pyridyl | 2-tetrahydrofuranylmethyl isomers A&B | 516 |
| 311 | C(O) | 2-pyridyl | benzyl | 506 |
| 312 | C(O) | 5-fluoro-2-pyridyl | 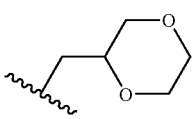 | 516 |
| 313 | C(O) | 5-chloro-2-pyridyl | 2-tetrahydrofuranylmethyl | 516 |
| 314 | C(O) | 2-pyridyl | 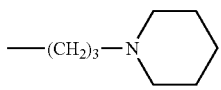 | 498 |
| 315 | C(O) | 5-chloro-2-pyridyl | CH$_3$ | 446 |
| 316 | C(O) | pyrazinyl | 2-tetrahydrofuranylmethyl | 483 |
| 317 | C(O) | 3-pyridazinyl | 2-tetrahydrofuranylmethyl | 483 |

TABLE 5

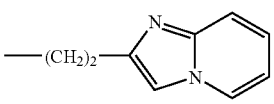

| Ex. | A | R¹ᵃ/R¹ᵇ | R⁴ | MS |
|---|---|---|---|---|
| 318 | C(O) | H/H | 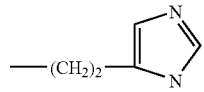 | 521 |
| 319 | C(O) | H/H |  | 540 |
| 320 | C(O) | H/H | 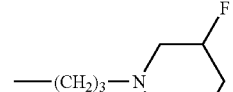 | 490 |
| 321 | C(O) | H/H | 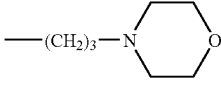 | 504 |
| 322 | C(O) | H/H | 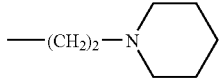 | 539 |
| 323 | C(O) | H/H | 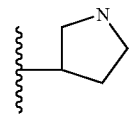 | 523 |
| 324 | C(O) | 4-F | 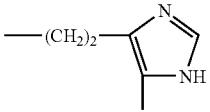 | 525 |
| 325 | C(O) | H/H | 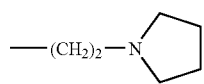 | 502 |
| 326 | C(O) | H/H | 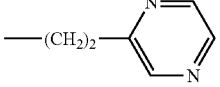 | 504 |
| 327 | C(O) | H/H | —(CH$_2$)$_2$—N<pyrrolidine> | 493 |
| 328 | C(O) | H/H | —(CH$_2$)$_2$—pyrazinyl | 502 |

TABLE 5-continued

| Ex. | A | R1a/R1b | R4 | MS |
|---|---|---|---|---|
| 329 | C(O) | H/H | 3-pyrrolidinyl (N-H) | 465 |
| 330 | C(O) | H/H | —CH2-(1,3-dioxan-2-yl) | 496 |
| 331 | C(O) | H/H | —CH2-(tetrahydropyran-2-yl) | 494 |
| 332 | C(O) | H/H | —(CH2)2-piperidin-1-yl | 507 |
| 333 | C(O) | H/H | —(CH2)3-(3,3-difluoropiperidin-1-yl) | 557 |
| 334 | C(O) | H/H | —(CH2)2-imidazo[2,1-b]thiazol-6-yl | 545 |
| 335 | C(O) | 2,4-diCl | —(CH2)2-piperidin-1-yl | 564 |
| 336 | C(O) | H/H | —(CH2)2-(tetrahydropyran-4-yl) | 508 |
| 337 | C(O) | H/H | —(CH2)2-(tetrahydrofuran-2-yl) | 494 |
| 338 | C(O) | H/H | 3-piperidinyl (N-H) | 479 |
| 339 | C(O) | H/H | —CH2-imidazo[1,2-a]pyridin-3-yl | 526 |
| 340 | C(O) | H/H | —(CH2)2-morpholin-4-yl | 509 |
| 341 | C(O) | H/H | 3-pyrrolidinyl (NH) | 465 |
| 342 | C(O) | H/H | —(CH2)2-pyridin-4-yl | 501 |
| 343 | C(O) | H/H | —(CH2)2-pyridin-2-yl | 501 |
| 344 | C(O) | H/H | —CH2-(tetrahydrofuran-2-yl) | 480 |
| 345 | C(O) | 4-F | CO2CH2CH3 | 486 |
| 346 | C(O) | H/H | —(CH2)2C(O)—(1,1-dioxothiomorpholin-4-yl) | 585 |
| 347 | C(O) | H/H | —(CH2)2-(tetrahydropyran-2-yl) | 508 |
| 348 | C(O) | H/H | —(CH2)2-morpholin-4-yl | 509 |
| 349 | C(O) | H/H | —CH2-pyrrolidin-2-yl | 516 |
| 350 | C(O) | H/H | —(CH2)2NHCH3 | 453 |
| 351 | C(O) | H/H | —(CH2)2C(O)-morpholin-4-yl | 537 |
| 352 | C(O) | H/H | —CH2-(tetrahydrofuran-3-yl) | 480 |
| 353 | C(O) | H/H | —(CH2)2-pyridin-3-yl | 501 |
| 354 | C(O) | H/H | —(CH2)2OCH3 | 454 |
| 355 | C(O) | H/H | —(CH2)2OCH3 | 468 |

TABLE 5-continued

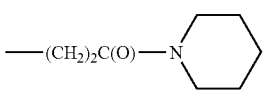

| Ex. | A | R1a/R1b | R4 | MS |
|---|---|---|---|---|
| 356 | C(O) | H/H | —(CH2)2C(O)—N-piperidine | 536 |
| 357 | C(O) | H/H | —CH2CO2C(CH3)3 | 510 |
| 358 | C(O) | H/H | —CH2-imidazole | 493 |
| 359 | C(O) | H/H | —CH2-imidazo[1,2-a]pyrimidine | 527 |
| 360 | C(O) | H/H | —(CH2)2-1,2,4-triazole | 491 |
| 361 | C(O) | H/H | —(CH2)2-thiazole | 507 |
| 362 | C(O) | H/H | —(CH2)2—C(O)—N(3-fluoropiperidine) | 553 |
| 363 | C(O) | H/H | —CH2-(5-methylimidazole) | 490 |
| 364 | C(O) | H/H | —C(O)-tetrahydrofuran | 494 |
| 365 | C(O) | H/H | —(CH2)3Cl | 472 |
| 366 | C(O) | H/H | —CO2CH2CH3 | 468 |
| 367 | C(O) | H/H | 1-benzylpiperidin-3-yl | 569 |
| 368 | C(O) | H/H | —CH2-imidazo[1,2-a]pyridine | 526 |
| 369 | C(O) | H/H | —CH2-(1H-1,2,4-triazol-3-yl) | 477 |
| 370 | C(O) | H/H | cyclohexyl | 478 |
| 371 | C(O) | H/H | —(CH2)2—C(O)—N(3,3-difluoropiperidine) | 571 |
| 372 | C(O) | H/H | —(CH2)2-benzimidazole | 540 |
| 373 | C(O) | H/H | —(CH2)2NHOOCH3 | 481 |
| 374 | C(O) | H/H | 1-acetyl-3-methylpiperidin-yl | 521 |
| 375 | C(O) | H/H | —CH2-pyrazolo[1,5-a]pyridine | 526 |
| 376 | C(O) | H/H | —(CH2)2CO2C(CH3)3 | 524 |
| 377 | C(O) | H/H | 3-pyridyl | 473 |
| 378 | C(O) | H/H | —(CH2)2-benzotriazole | 541 |
| 379 | C(O) | H/H | —(CH2)2N(CH3)CO2C(CH3)3 | 553 |
| 380 | C(O) | H/H | —CH2CH2CH3 | 438 |
| 381 | C(O) | H/H | —(CH2)3Ph | 514 |
| 382 | C(O) | H/H | 1-(CO2C(CH3)3)pyrrolidin-3-yl | 565 |
| 383 | C(O) | H/H | —(CH2)2N(CH3)2 | 467 |
| 384 | C(O) | H/H | —CH2CONH2 | 453 |
| 385 | C(O) | H/H | —CH2CH3 | 424 |
| 386 | C(O) | H/H | —CH2CH2Cl | 458 |
| 387 | C(O) | H/H | CH3 | 410 |
| 388 | C(O) | H/H | —C(O)CH3 | 438 |
| 389 | C(O) | H/H | cyclopropyl | 436 |

TABLE 5-continued

| Ex. | A | $R^{1a}/R^{1b}$ | $R^4$ | MS |
|---|---|---|---|---|
| 390 | C(O) | H/H | (3-piperidinyl, N-CO₂C(CH₃)₃) | 579 |
| 391 | C(O) | H/H | —(CH₂)₂—C₆H₄—CN | 525 |
| 392 | C(O) | H/H | 5-indolyl | 511 |
| 393 | C(O) | H/H | —C(CH₃)₃ | 452 |
| 394 | C(O) | H/H | —CH₂-(2-pyrrolidinyl, N-CO₂C(CH₃)₃) | 579 |
| 395 | C(O) | H/H | 2-pyridyl | 473 |
| 396 | C(O) | H/H | 6-indolyl | 511 |
| 397 | C(O) | H/H | CH₃ | 467 |
| 398 | C(O) | H/H | phenyl | 472 |

What is claimed is:

1. A compound of formula I and pharmaceutically acceptable salts thereof:

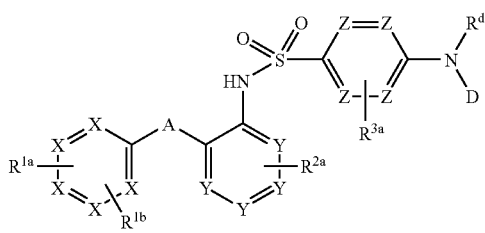

I wherein

A is O, CO, S, $NR^d$, or $CR^bR^c$;

D is $COR^4$, $C(O)NR^dR^4$, $C(O)OR^4$;

X, Y and Z are independently a ring carbon atom or a ring nitrogen atom, with the proviso that 0-3 X, 0-3 Y and 0-3 Z are ring nitrogen atoms;

$R^{1a}$ and $R^{1b}$ are independently selected from (1) H, (2) halogen, (3) $C_{1-6}$alkyl optionally substituted with 1-5 groups independently selected from halogen, nitro, cyano, $COR^a$, $CO_2R^a$, $C(O)NR^dR^e$, $OR^a$, $OC(O)R^a$, $SR^a$, $SO_2R^f$, $S(O)R^f$, $NR^dR^e$, $NR^dC(O)R^a$ and $NR^dSO_2R^f$, (4) $C(O)R^a$, (5) $CO_2R^a$, (6) $C(O)NR^dR^e$, (7) $OR^a$, (8) $OC(O)R^a$, (9) $OC(O)NR^dR^e$, (10) $NR^dR^e$, (11) $NR^dC(O)R^a$, (12) $NR^dC(O)OR^a$, (13) $NR^dC(O)NR^dR^e$, (14) $NR^dSO_2R^f$, (15) $SR^a$, (16) $S(O)R^f$, (17) $SO_2R^f$, (18) $SO_2NR^dR^e$, (19) CN, (20) $NO_2$, (21) optionally substituted aryl, (22) optionally substituted heteroaryl, (23) optionally substituted heterocyclyl, (24) optionally substituted aryl-$C_{1-6}$alkyl, (25) optionally substituted heteroaryl-$C_{1-6}$alkyl, and (26) optionally substituted heterocyclyl-$C_{1-6}$alkyl; wherein the substituents for aryl, heteroaryl, heterocyclyl, aralkyl, heteroaralkyl and heterocyclylalkyl are 1 to 3 groups independently selected from halogen, cyano, nitro, $OR^a$, $NR^dR^e$, $NR^dC(O)R^a$, $NR^dSO_2R^f$, $OC(O)R^a$, $NR^dC(O)_2R^a$, $SR^a$, $SO_2R^f$, oxo (for heterocyclyl and heterocyclylalkyl), $C(O)R^a$, $C(O)_2R^a$, $C_{1-4}$alkyloxy, aryl, aryl-$C_{1-4}$alkyl, heteroaryl, heteroaryl-$C_{1-4}$alkyl, $C_{3-6}$cycloalkyl and $C_{1-4}$alkyl optionally substituted with 1 to 5 halogen atoms, or $R^{1a}$, $R^{1b}$ and adjacent carbon atoms to which they are attached together form a saturated, partially unsaturated or aromatic 5- or 6-membered ring containing 0 to 2 heteroatoms selected from N, N—$R^g$, O and S;

$R^{2a}$ and $R^{3a}$ are independently selected from (1) H, (2) halogen, (3) $OR^a$, (4) $NR^dR^e$, (5) CN, (6) $NO_2$, (7) $CO_2R^a$, (8) $COR^a$, and (9) $C_{1-4}$alkyl optionally substituted with 1 to 5 halogen atoms, $R^4$ is selected from (1) $C_{1-6}$alkyl substituted with 1 to 5 halogen atoms, $OR^a$, $NR^dR^e$ or $C(O)NR^dR^e$ in which, for these two occurrences, $R^d$ and $R^e$ together complete a 4- to 8-membered ring optionally containing an additional heteroatom selected from $NR^g$, O, S, and $SO_2$, and said ring being optionally fused to a benzene or a 5- or 6-membered heteraromatic ring, and optionally substituted with 1 to 3 substituents independently selected from halogen, cyano, nitro, $OR^g$, oxo. $C_{3-6}$cycloalkyl, aryl, heteroaryl, $NR^gR^g$, $NR^gCOR^g$, $NR^gCO_2R^g$ and $C_{1-4}$alkyl optionally substituted with 1 to 5 halogen atoms; (2) optionally substituted heteroaryl; (3) optionally substituted heteroaryl-$C_{1-4}$alkyl; (4) optionally substituted heterocyclyl; (5) optionally substituted heterocyclyl-$C_{1-4}$alkyl; wherein the substituents for heteroaryl, heteroaralkyl, heterocyclyl and heterocyclylalkyl are 1 to 3 groups independently selected from halogen, cyano, nitro, $OR^a$, $NR^dR^e$, $NR^dC(O)R^a$, $NR^dSO_2R^f$, $OC(O)R^a$, $NR^dC(O)_2R^a$, $SR^a$, $SO_2R^f$, oxo (for heterocyclyl and heterocyclylalkyl), $C(O)R^a$, $C(O)_2R^a$, $C_1$-4alkyloxy, aryl, aryl-$C_{1-4}$alkyl, heteroaryl, heteroaryl-$C_{1-4}$alkyl, $C_{3-6}$cycloalkyl and $C_{1-4}$alkyl optionally substituted with 1 to 5 halogen atoms;

$R^a$ is (1) H, (2) $C_{1-6}$alkyl optionally substituted with 1 to 5 groups independently selected from halogen, cyano, nitro, OH, $C_{1-4}$alkyloxy and $C_{3-6}$cycloalkyl, (3) $C_{3-6}$cycloalkyl, (4) optionally substituted aryl, (5) optionally substituted heterocyclyl, (6) optionally substituted heterocyclyl, (7) optionally substituted aryl-$C_{1-6}$alkyl, (8) optionally substituted heteroaryl-$C_{1-6}$alkyl, and (9) optionally substituted heterocyclyl-$C_{1-6}$alkyl; wherein the substituents for aryl, heteroaryl, heterocyclyl, aralkyl, heteroaralkyl and heterocyclylalkyl are 1 to 3 groups independently selected from halogen, cyano, nitro, $OR^g$, $NR^dR^e$, $NR^dC(O)R^g$, $NR^dSO_2R^f$, $OC(O)R^g$, $NR^dC(O)_2R^g$, $SR^g$, $SO_2R^f$, oxo (for heterocyclyl and heterocyclylalkyl), $C(O)Rg^a$, $C(O)_2R^g$, $C_{1-4}$alkyloxy, aryl, aryl-$C_{1-4}$alkyl, heteroaryl, heteroaryl-$C_{1-4}$alkyl, $C_{3-6}$cycloalkyl and $C_{1-4}$alkyl optionally substituted with 1 to 5 halogen atoms;

$R^b$ and $R^c$ are independently selected from H, halogen, or $C_{1-4}$alkyl optionally substituted with 1 to 5 halogen atoms;

$R^d$ and $R^e$ are independently selected from (1) H, (2) $C_{1-4}$alkyl, optionally substituted with 1 to 5 groups independently selected from halogen, amino, mono-$C_{1-4}$alkylamino, di-$C_{1-4}$alkylamino, and $SO_2R^f$, (3) aryl-$C_{1-6}$alkyl optionally substituted with 1 to 3 groups selected from halogen, cyano, nitro, OH, $C_{1-4}$alkyloxy, $C_{3-6}$cycloalkyl and $C_{1-4}$alkyl optionally substituted with 1 to 5 halogen atoms, (4) heteroaryl-$C_{1-6}$alkyl optionally substituted with 1 to 3 groups selected from halogen, cyano, nitro, OH, $C_{1-4}$alkyloxy, $C_{3-6}$cycloalkyl and $C_{1-4}$alkyl optionally substituted with 1 to 5 halogen atoms, and (5) $C_{3-6}$cycloalkyl, or $R^d$ and $R^e$, or $R^d$ and $R^4$, together with the atom or atoms to which they are attached, complete a 4- to 8-membered saturated, partially saturated or aromatic ring optionally containing 1 to 3 heteroatoms independently selected from N, $NR^g$, O, S, and $SO_2$, and said ring being optionally fused to a benzene or a 5- or 6-membered hetearomatic ring, and optionally substituted with 1 to 3 substituents independently selected from halogen, cyano, nitro, $OR^g$, oxo, $C_{3-6}$cycloalkyl, aryl, aryl-$C_{1-4}$alkyl, heteroaryl, $NR^gR^g$, $NR^gCOR^g$, $NR^gCO_2R^g$ and $C_{1-4}$alkyl optionally substituted with 1 to 5 halogen atoms;

$R^f$ is selected from (1) $C_{1-4}$alkyl optionally substituted with 1 to 5 halogen atoms, (2) $C_{1-4}$alkyloxy, and (3) aryl optionally substituted with 1 to 3 groups selected from halogen, cyano, nitro, OH, $C_{1-4}$alkyloxy, $C_{3-6}$cycloalkyl and $C_{1-4}$alkyl optionally substituted with 1 to 5 halogen atoms;

$R^g$ is selected from (1) H, (2) $C_{1-4}$alkyl, (3) aryl, (4) aryl-$C_{1-6}$alkyl, (5) $C(O)_2C_{1-4}$alkyl and (6) $C(O)C_{1-4}$alkyl.

2. A compound of claim 1 wherein A is C(O) or O.

3. A compound of claim 1 wherein each occurrence of Y and Z represents a ring carbon atom, and one X is a ring carbon or nitrogen atom and the others are ring carbon atoms.

4. A compound of claim 1 having the formula Ia(1) and pharmaceutically acceptable salts thereof:

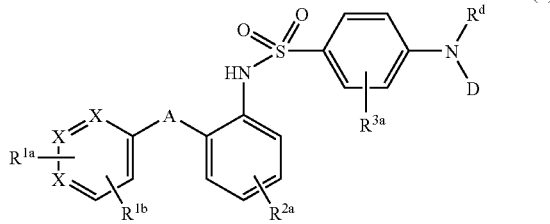

Ia(1)

wherein
A is O or C(O);
one of X is a ring carbon or nitrogen atom, and the others are ring carbon atoms;
$R^{1a}$ and $R^{1b}$ are independently selected from hydrogen, halogen, $C_{1-4}$alkyl, cyano, $SR^a$, $OR^a$ and $CF_3$;
$R^{2a}$ and $R^{3a}$ are independently H or halogen;
$R^4$ is selected from (1) $C_{1-4}$alkyl substituted with one to 5 groups independently selected from halogen, $C_{3-6}$cycloalkyl, $NR^dR^e$, $NR^dC(O)_2R^a$, $C(O)NR^dR^e$, $C(O)OR^a$, and $OR^a$; (2) $C_{3-6}$cycloalkyl; (3) phenyl: (4) phenyl-$C_{1-4}$alkyl; (5) optionally substituted heteroaryl; (6) optionally substituted heteroaryl-$C_{1-4}$alkyl; (7) optionally substituted heterocyclyl; and (8) optionally substituted heterocyclyl-$C_{1-4}$alkyl; wherein heteroaryl, including as part of heteroarylalkyl, is selected from benzofuranyl, pyrazolo[1,5-a]pyrimidinyl, 1-azaindolizinyl, s-triazolo[1,5-a]pyrimidinyl, thieno[3,2-b]pyridinyl, isoxazolyl, pyrazinyl, pyrazolyl, pyrimidinyl, benzisoxazolyl, pyridyl, indolyl, benzimidazolyl, benzthiazolyl and imidazo[2,1-b]thiazolyl; heterocyclyl, including as part of heterocyclylalkyl, is selected from morpholinyl, tetrahydropyranyl, tetrahydrofuranyl, pyrrolidinyl, piperidinyl and imidazolidinyl; the substituents for heteroaryl is 1 or 2 groups independently selected from $C_{1-4}$alkyl, $C_{3-6}$cycloalkyl, and $OR^a$; and the substituents for heterocyclyl is 1 to 3 groups independently selected from oxo and $C_{1-4}$alkyl, $R^a$ and $R^d$ are as defined in claim 1.

5. A compound of claim 4 wherein $R^4$ is selected from (1) $C_{1-4}$alkyl substituted with $NR^dR^e$ or $C(O)NR^dR^e$ where for both groups $R^d$ and $R^e$, together with the nitrogen atom to which they are attached, complete an optionally substituted 5- or 6-membered saturated ring having 0 to 1 additional ring heteroatom selected from $NR^g$, O, S and $SO_2$, and wherein said substituent is 1 or 2 groups independently selected from $OR^a$, halogen, $C_{1-4}$alkyl and oxo; (2) optionally substituted heteroaryl wherein said heteroaryl is selected from pyrazolyl, isoxazolyl, pyrimidinyl, benzofuranyl, pyrazolo[1,5-a]pyrimidinyl, 1-azaindolizinyl, s-triazolo[1,5-a]pyrimidinyl, imidazo[2,1-b]thiazolyl, thieno[3,2-b]pyridinyl, and said substituent is 1 to 3 groups independently selected from furanyl, pyridyl, benzyl, phenyl optionally substituted with halogen, $C_{1-4}$alkyl, $C_{3-6}$cycloalkyl, trifluoromethyl, halogen, and $C_{1-4}$alkoxy.

6. A compound of claim 1 having a formula Ia(2) and pharmaceutically salts thereof:

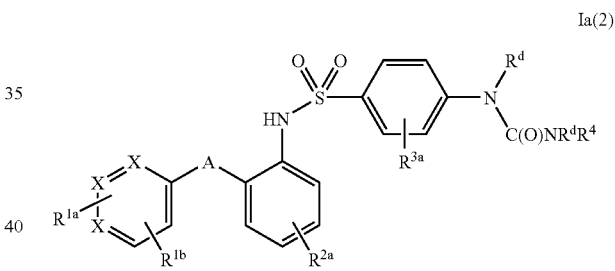

Ia(2)

wherein $R^d$ is H and $R^4$ is selected from (1) $C_{1-4}$alkyl substituted with a group selected from halogen, $OR^a$, $CO_2R^a$, $NHCOR^a$, $NR^dR^e$ and $C(O)NR^dR^e$; (2) optionally substituted heteroaryl-$C_{1-4}$alkyl wherein heteroaryl is selected from azaindolizinyl, imidazolyl, benzimidazolyl, pyrazinyl, pyridyl, indolyl, triazolyl, thiazolyl, imidazo[1,2-a]pyridyl, imidazo[1,2-a]pyrimidinyl, imidazo[2,1-b]thiazolyl, and pyrazolo[1,5-a]-pyrimidinyl; (3) optionally substituted heterocycylyl-$C_{1-4}$alkyl wherein heterocyclyl is selected from tetrahydropyranyl, tetrahydrofuranyl and dioxanyl; (4) optionally substituted heterocyclyl selected from pyrrolidinyl and piperidinyl; (5) $CO_2R^a$; (6) $C_{3-6}$cycloalkyl; and (7) optionally substituted phenyl-$C_{1-4}$alkyl; or $R^d$ and $R^4$ together with the nitrogen atom to which they are attached complete an optionally substituted 5- or 6-membered saturated ring having 0 to 1 additional ring heteroatom selected from $NR^g$, O, S and $SO_2$, wherein said ring is optionally fused to a benzene or a 5- or 6-membered heteroaryl ring, and said substituent is 1 or 2 groups independently selected from $OR^a$, halogen, $C_{1-4}$alkyl, $NR^dR^e$, $NR^dCO2R^a$, and oxo.

7. A compound of claim 6 wherein $R^d$ is H and $R^4$ is selected from (1) $C_{1-4}$alkyl substituted with $NR^dR^e$ or $C(O)NR^dR^e$, wherein for both groups $R^d$ and $R^e$ together with the nitrogen to which they are attached complete an optionally substituted 5- or 6-membered saturated ring having 0 to 1 additional ring heteroatom selected from $NR^g$, O, S and $SO_2$, and wherein said substituent is 1 or 2 groups independently selected from $OR^a$, halogen, $C_{1-4}$alkyl and oxo; (2) heterocyclyl or heterocyclyl-$C_{1-4}$alkyl wherein said heterocyclyl is selected from pyrrolidinyl, 1,4-dioxanyl, and tetrahydropyranyl; and (3) heteroaryl-$C_{1-4}$alkyl optionally substituted with 1 to 3 $C_{1-4}$-alkyl groups, wherein said heteroaryl is selected from imidazolyl, 1-azaindolizinyl, imidazo[2,1-b]thiazolyl, and pyrimidinyl.

8. A compound of claim 1 having the formula Ia(3) an pharmaceutically acceptable salts thereof:

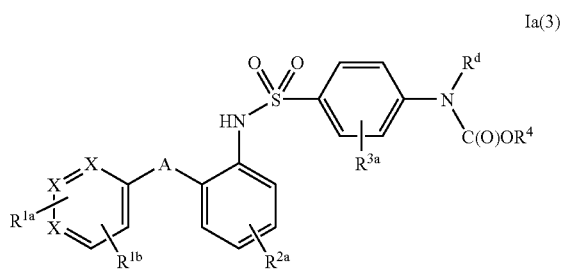

Ia(3)

wherein $R^4$ is selected from (1) $C_{2-4}$alkyl substituted with $NR^dR^e$ or $C(O)NR^dR^e$ in which, for these two groups, $R^d$ and $R^e$ together with the nitrogen atom to which they are attached complete an optionally substituted 5- or 6-membered saturated ring having 0 to 1 additional ring heteroatom selected from $NR^g$, O, S and $SO_2$, and wherein said substituent is 1 or 2 groups independently selected from $OR^a$, halogen, $C_{1-4}$alkyl and oxo; (2) heterocyclyl-$C_{1-4}$alkyl optionally substituted with 1 to 3 groups independently selected from $C_{1-4}$alkyl and oxo, wherein heterocyclyl is selected from tetrahydropyranyl, tetrahydrofuranyl, pyrrolidinyl, morpholinyl, oxazolidinyl, dioxanyl, and dioxolanyl; (3) furanyl-$C_{1-4}$alkyl; and (4) phenyl-$C_{1-4}$alkyl.

9. A pharmaceutical composition comprising a therapeutically effective amount of a compound of formula I, or a pharmaceutically acceptable salt thereof, and pharmaceutically acceptable excipients.

10. A method for the treatment of diseases or disorders mediated through the bradykinin receptor pathway which comprises administering to a patient in need thereof a compound of formula I or a pharmaceutically acceptable salt thereof.

11. The method of claim 10 wherein said disease or disorder is selected from neuropathic pain, acute pain and inflammatory pain.

* * * * *